(12) United States Patent
Becker et al.

(10) Patent No.: US 8,833,565 B2
(45) Date of Patent: Sep. 16, 2014

(54) APPARATUS AND METHOD FOR SEED SELECTION

(75) Inventors: Steven M. Becker, Johnston, IA (US); Jason M. Cope, Ankeny, IA (US); James Dimond, Ames, IA (US); Joshua L. Mongan, Saint Charles, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 715 days.

(21) Appl. No.: 13/113,673

(22) Filed: May 23, 2011

(65) Prior Publication Data

US 2011/0297589 A1 Dec. 8, 2011

Related U.S. Application Data

(60) Provisional application No. 61/352,674, filed on Jun. 8, 2010.

(51) Int. Cl.
| | |
|---|---|
| *B07C 5/34* | (2006.01) |
| *G01N 35/00* | (2006.01) |
| *A01H 1/04* | (2006.01) |
| *A01C 1/00* | (2006.01) |
| *B07C 5/36* | (2006.01) |
| *G01N 1/28* | (2006.01) |
| *G01N 33/00* | (2006.01) |

(52) U.S. Cl.
CPC ............ *G01N 1/286* (2013.01); *G01N 35/0099* (2013.01); *A01H 1/04* (2013.01); *A01C 1/00* (2013.01); *B07C 5/36* (2013.01); *G01N 2033/0077* (2013.01)
USPC ..................................... 209/552; 47/58.1 SE

(58) Field of Classification Search
USPC .............. 209/552, 909; 47/14, 58.1, 58.1 LS, 47/58.1 SE
See application file for complete search history.

(56) References Cited

U.S. PATENT DOCUMENTS

| 3,195,485 A | 7/1965 | Reynolds |
| 3,530,372 A | 9/1970 | Laukien |

(Continued)

FOREIGN PATENT DOCUMENTS

| DE | 196 16 216 A1 | 10/1997 |
| EP | 1 346 206 B1 | 9/2003 |

(Continued)

OTHER PUBLICATIONS

Aitken-Christie, J. et al., *Automation in Plant Tissue Culture*, Automation and Environmental Control in Plant tissue Culture (1995) 1-18.

(Continued)

*Primary Examiner* — Joseph C Rodriguez
(74) *Attorney, Agent, or Firm* — Pioneer Hi-Bred Int'l, Inc.

(57) ABSTRACT

Apparatuses and methods for selecting one or more seeds from a group of seeds based on a predetermined characteristic of the selected seeds are provided. In various embodiments, the seeds are selected from multiple containers of seeds and re-configured into a single container for later use. The apparatus includes an array of seed selectors that expel the selected seeds from the corresponding compartments through contact with the compartments. A transfer member then directs each expelled seed to a cavity of a collection tray or into an envelope or other receptacle. A controller may run operation of the apparatus and associate the selected seeds with the cavities and/or receptacle into which they are deposited. In this way, numerous seeds may be automatically selected substantially simultaneously or in rapid succession and re-configured in a short period of time and with limited user intervention.

12 Claims, 17 Drawing Sheets

(56) References Cited

U.S. PATENT DOCUMENTS

| | | | |
|---|---|---|---|
| 3,572,548 | A | 3/1971 | Fuchs |
| 4,230,983 | A | 10/1980 | Steere et al. |
| 4,602,716 | A | 7/1986 | Barla-Szabo et al. |
| 5,677,474 | A | 10/1997 | Rogers |
| 6,307,123 | B1 | 10/2001 | Kriz et al. |
| 6,537,826 | B1 | 3/2003 | Horigane |
| 6,705,827 | B2 | 3/2004 | Keller et al. |
| 6,706,989 | B2 | 3/2004 | Hunter et al. |
| 6,809,819 | B1 | 10/2004 | Vinjamoori et al. |
| 6,865,556 | B2 | 3/2005 | Penner et al. |
| 6,959,617 | B2 | 11/2005 | Deppermann |
| 7,044,306 | B2 | 5/2006 | Deppermann |
| 7,067,834 | B2 | 6/2006 | Horigane et al. |
| 7,290,665 | B2 | 11/2007 | Hunter et al. |
| 7,367,155 | B2 | 5/2008 | Kotyk et al. |
| 7,502,113 | B2 | 3/2009 | Deppermann et al. |
| 7,588,151 | B2 | 9/2009 | Hunter et al. |
| 7,591,101 | B2 | 9/2009 | Deppermann |
| 7,591,374 | B2 | 9/2009 | Hunter et al. |
| 7,600,642 | B2 | 10/2009 | Deppermann et al. |
| 7,611,842 | B2 | 11/2009 | Deppermann et al. |
| 7,685,768 | B2 | 3/2010 | Deppermann et al. |
| 7,703,238 | B2 | 4/2010 | Deppermann et al. |
| 7,767,883 | B2 | 8/2010 | Deppermann et al. |
| 7,830,516 | B2 | 11/2010 | Deppermann et al. |
| 7,832,143 | B2 | 11/2010 | Deppermann et al. |
| 7,849,632 | B2 | 12/2010 | Deppermann et al. |
| 7,877,926 | B2 | 2/2011 | Deppermann et al. |
| 7,905,050 | B2 | 3/2011 | Hunter et al. |
| 7,934,600 | B2 | 5/2011 | Deppermann et al. |
| 7,941,969 | B2 | 5/2011 | Deppermann et al. |
| 7,997,415 | B2 * | 8/2011 | Mongan et al. ............... 209/213 |
| 7,998,669 | B2 | 8/2011 | Deppermann et al. |
| 8,028,469 | B2 | 10/2011 | Deppermann et al. |
| 8,031,910 | B2 | 10/2011 | Jones et al. |
| 8,033,426 | B2 * | 10/2011 | Becker et al. .................. 222/52 |
| 8,071,845 | B2 | 12/2011 | Deppermann et al. |
| 8,076,076 | B2 | 12/2011 | Osborn et al. |
| 8,245,439 | B2 | 8/2012 | Deppermann et al. |
| 8,281,935 | B2 | 10/2012 | Deppermann et al. |
| 2004/0267457 | A1 | 12/2004 | Timmis et al. |
| 2005/0082207 | A1 | 4/2005 | Deppermann |
| 2006/0042527 | A1 | 3/2006 | Deppermann |
| 2006/0046244 | A1 | 3/2006 | Deppermann |
| 2007/0048872 | A1 | 3/2007 | Deppermann et al. |
| 2007/0207485 | A1 | 9/2007 | Deppermann et al. |
| 2008/0000815 | A1 | 1/2008 | Deppermann |
| 2008/0131254 | A1 | 6/2008 | Cope et al. |
| 2008/0131924 | A1 | 6/2008 | Cope et al. |
| 2008/0317279 | A1 | 12/2008 | Deppermann et al. |
| 2009/0061449 | A1 | 3/2009 | Chung et al. |
| 2009/0155878 | A1 | 6/2009 | Becker et al. |
| 2009/0215060 | A1 | 8/2009 | Deppermann et al. |
| 2009/0320955 | A1 | 12/2009 | Becker et al. |
| 2010/0043685 | A1 | 2/2010 | Gogerty et al. |
| 2010/0044356 | A1 | 2/2010 | Cope |
| 2010/0044381 | A1 * | 2/2010 | Goldman ...................... 220/507 |
| 2010/0047912 | A1 | 2/2010 | Mongan et al. |
| 2010/0086963 | A1 | 4/2010 | Deppermann et al. |
| 2010/0299790 | A1 | 11/2010 | Deppermann et al. |
| 2011/0081716 | A1 | 4/2011 | Deppermann et al. |
| 2011/0117570 | A1 * | 5/2011 | Cope et al. .......... 435/6 |
| 2011/0129836 | A1 | 6/2011 | Deppermann et al. |
| 2011/0160068 | A1 * | 6/2011 | Becker et al. ...................... 506/7 |
| 2011/0217700 | A1 | 9/2011 | Deppermann et al. |
| 2011/0225680 | A1 | 9/2011 | Cope |
| 2011/0296930 | A1 | 12/2011 | Deppermann et al. |
| 2011/0309102 | A1 * | 12/2011 | Becker et al. ...................... 222/1 |
| 2012/0073416 | A1 * | 3/2012 | Becker et al. ...................... 83/23 |
| 2012/0079629 | A1 | 3/2012 | Deppermann et al. |
| 2012/0180386 | A1 | 7/2012 | Deppermann et al. |
| 2013/0205660 | A1 * | 8/2013 | Deppermann et al. ... 47/58.1 SE |
| 2014/0020287 | A1 * | 1/2014 | Deppermann et al. ............ 47/14 |

FOREIGN PATENT DOCUMENTS

| | | |
|---|---|---|
| EP | 1 391 713 A2 | 2/2004 |
| FR | 2 825 467 | 12/2002 |
| GB | 2 293 744 A | 4/1996 |
| KR | 10-2000-0022775 | 11/2001 |
| KR | 339689 B | 6/2002 |
| RU | 1805835 A3 | 3/1993 |
| RU | 2187919 C2 | 8/2002 |
| WO | WO 03/084847 A2 | 10/2003 |
| WO | WO 2006/026466 A2 | 3/2006 |
| WO | WO 2006/026467 A2 | 3/2006 |
| WO | WO 2007/025250 A2 | 3/2007 |
| WO | WO 2007/103769 A2 | 9/2007 |
| WO | WO-2007/103786 A2 | 9/2007 |
| WO | WO 2007/103786 A2 | 9/2007 |
| WO | WO-2008/150798 A1 | 12/2008 |
| WO | WO 2008/150798 A1 | 12/2008 |
| WO | WO 2009/032741 A2 | 3/2009 |

OTHER PUBLICATIONS

Casady, W. W. et al., *An Automated Kernel Positioning Device for Computer Vision Analysis of Grain*, American Society of Agricultural Engineers, vol. 32(5) (1989) 1821-1826.

Chunwongse, J. et al., *Pre-Germation Genotypic Screening Using PCR Amplification of Half-Seeds*, Theor Appl Genet, 86 (1993) 694-698.

Churchill, D. B. et al., *Rotating Table for Measuring Seed Physical Properties*, Transactions of the ASAE, vol. 34(4) (1991) 1842-1845.

Dekkers, J. C. M. et al., *The Use of Molecular Genetics in the Improvement of Agricultural Populations*, Nature Reviews | Genetics, vol. 3, (2002) 22-32.

Gasvoda, D. et al., *White Pine Seed Scarifier*, United States Department of Agriculture Food Service, Technology & Development Program, Timber Tech Tips, 0224-2332-MTDC (2002) pp. 1-6.

Hahnen, S. et al., *Automated DNA Preparation from Maize Tissues and Food Samples Suitable for Real-time PCR Detection of Native Genes*, European Food Research Technology, vol. 215 (2002) 443-446.

Higley, P.M., et al., *Effects of Non-Destructive Tissue Extraction on the Viability of Corn, Soybean and Bean Seeds*, Seed Sci & Technol., 22 (1994) 245-252.

Horigane, A. et al., *Evaluation of Color Characteristics of Cross-Sectioned Wheat Kernels*, Food Sci. Technol. Res., 9:4 (2003), 327-331.

Horigane, A. et al., *Measurement of Brightness of Cross-Sectioned Wheat Kernels*, Japanese Journal of Crop Science, vol. 72, (attachment No. 1) (2003).

Horigane, A. et al., *Two-Dimensional Analysis of Kernals Using a New Sample Preparation Method*, Chemistry and Biology, vol. 41, No. 6 (2003) 398-402.

Kamiya, M. et al., *Rapid DNA Extraction Method from Soybean Seeds*, Breeding Science 53 (2003) 277-279.

Kang, H.W. et al., *A Rapid DNA Extraction Method for RFLP and PCR Analysis from a Single Dry Seed*, Plant Molecular Biology Reporter, 16:90 (1998) 1 pg.

Kerk, N.M. et al., *Laser Capture Microdissection of Cells from Plant Tissues*, Plant Physiology, vol. 132 (2003) 27-35.

Krysan, P., *Ice-Cap. A High-Throughput Method for Capturing Plant Tissue Samples for Genotype Analysis*, Plant Physiology, vol. 135 (2004) 1162-1169.

Liu, W. et al., *Highly Efficient Doubled-Haploid Production in Wheat via Induced Microsphere Embryogenesis*, Crop Science, vol. 42 (2002) 686-692.

McCarthy, P.L. et al., *Rapid Identification of Transformed Wheat Using a Half-Seed PCR Assay*, BioTechniques 32 (2002) 560-564.

Pearson, T.C. et al., *Reduction of Aflation and Fumonisin Contamination in Yellow Corn by High-Speed Dual-Wavelength Sorting*, Cereal Chem. 81(4), (2004) 490-498.

Peterhansel, C. et al., *Quantitative Detection of Transgenic and Endogenous DNA Sequences in Seeds After Automated DNA Preparation*, Biomed Eng. Appl. Basis Commun. 16 (2004) 1-6.

(56) References Cited

OTHER PUBLICATIONS

Rafalkski, J. A., *Genetic Diagnostics in Plant Breading: RAPDs Microsatellites & Machines*, TIG, vol. 9, No. 8 (Aug. 1993) 275-280.

Sangtong, V. et al., *Serial Extraction of Endosperm Drillings (SEED)—A Method for Detecting Transgenes and Proteins in Single Viable Maize Kernels*, Plant Molecular Biology Reporter 19 (2001) 151-158.

Skinner, D. Z. et al., *Segregation and Conditioning Probability Association of Molecular Markers With Traits in Autotetraploid Alfalfa*, Molecular Breading, vol. 5 (2000) 295-306.

Smith, J. S. C. et al., *Genetic Purity and Testing Technologies for Seed Quality: A Company Perspective*, Seed Science Research 8 (1998) 285-293.

Sweeney, P. et al., *Random Amplified Polymorphic DNA Analysis of Dry Turfgrass Seed*, HortScience 31(3), (1996) 400-401.

Turner, N.A., et al., *Sampling and Analysis for Determining Relationship of Calcium Concentration to Bitter Pit in Apple Fruit*, New Zealand Journal of Agriculture Research 20:4 (1977) 525-532.

Von Post, R. et al.,*A High-throughput DNA Extraction Method for Barley Seed*, Euphytica, 130 (2003) 255-260.

Wang, G.L., et al., *PCR Amplification from Single Seeds, facilitating DNA Marker-Assisted Breeding*, Nucleic Acids Research 21(10), (1993) 2527.

Wenxue, Z., et al.,*PCR Analysis of Half-Seeds of Cereal Crops and Its Applications in Marker-assisted Selection and Breeding*, Chinese Journal of Biotechnology, 12:4 (1997) 249-255.

Xu, Y., *Developing Marker-Assisted Selection Strategies for Breeding Hybrid Rice*, Plant Breeding Review, 23 (2003) 73-174.

Yang, W, et al., *A Preliminary Study of Non-Lethal Speciifc Sampling of Corn Embryo and Endosperm and Feasibility of Automating the Seed Selection Process Utilizing the Specific Sampling Technique*, Pioneer Hi-Bred (2002) 1-41

Wang, J. et al., *Identification of Parents of F1 Hybrids Through SSR Profiling of Material and Hybrid Tissue*, Euphytica, vol. 124 (2002) 29-34.

Yao, Y. et al., *Single Kernel Sampling Method for Maize Starch Analysis While Maintaining Kernel Vitality*, Cereal Chem. 79:6 (2002) 757-762.

DuPont CoatingSolutions [online] [retreived Apr. 4, 2013]. Retreived from the Internet: <URL: www.ccaiweb.com/PDF/MembersOnly/annualpres08//DuPontCoatingSolutions—Corporate Member Presentation.pdf>. (undated) 12 pages.

200 watt CO2 lasre from Synrad provides the best cost per delivered watt available in today . . . [online] [retrieved Dec. 18, 2012]. Retrieved from the Internet: <URL: http://www.synrad.com/fseries/f201.htm>. (2011) 2 pages.

Skinner, D. Z. et al., *Segregation and Conditioning Probability Association of Molecular Markers With Traits in Autotetraploid Alfalfa*, Molecular Breading, vol. 6 (2000) 295-306.

International Preliminary Report on Patentability and Written Opinion for International Application No. PCT/US2011/038686 dated Dec. 20, 2012.

International Search Report and Written Opinion for Application No. PCT/US2011/038686 dated Aug. 16, 2011.

\* cited by examiner

APPARATUS AND METHOD FOR SEED SELECTION

CROSS-REFERENCE TO RELATED APPLICATIONS

The present application claims priority from U.S. Provisional Application No. 61/352,674 filed Jun. 8, 2010, which is hereby incorporated herein by reference in its entirety.

FIELD OF THE INVENTION

The present invention relates generally to apparatuses and methods for selecting and packaging seeds and seed portions for further processing and/or handling. More specifically, the present invention provides an apparatus and method for selecting one or more seeds or seed portions having desired characteristics from a group of seeds and arranging the selected seeds in another container for downstream use.

BACKGROUND OF THE INVENTION

There are a wide variety of applications where seeds need to be stored, protected and preserved, and at some time later be easily, efficiently, and accurately identified and/or possibly individually selected, retrieved or discharged from one or more containers for reconfiguration into another container based upon the presence or absence of at least one advantageous property associated with the seed.

One notable example of this can be found in research and development directed to identifying and perpetuating advantageous seed properties. For instance, plant researchers often classify seeds in specific groups. In the case of seeds, a test portion (e.g., a piece, sample, or chip from the seed) may be removed from the seed for testing, and the remaining portion may be a viable seed portion that can be stored collectively with other viable seed portions or individually to protect against degradation or harm and to maintain viability. The viable seed portion in such cases may be capable of being planted to produce a plant bearing characteristics corresponding to the characteristics identified during analysis of the respective seed portion. The information learned from analyzing the test portions may indicate if the remaining, viable portion of a particular seed has desired properties as a result of a biological trait, a genetic trait, a phenotypic trait, a morphological trait, or pedigree.

Furthermore, the information learned from analyzing the test portion can be linked with the individual seed from which it originated (e.g., the viable seed portion) using an indexing system to correlate the two seed parts. Thus, by comparing a seed selection criterion with the information known about the seed, the remaining viable seed portion may be accurately identified, recovered, and used to produce plants exhibiting the desired characteristics.

As a result, there is a need for a high throughput apparatus and method that can easily, efficiently, and accurately select certain stored seeds or seed portions from a group of seeds or seed portions according to their predetermined characteristics and provide the selected seeds or seed portions in a usable manner for further processing.

BRIEF SUMMARY OF VARIOUS EMBODIMENTS

The present invention addresses the above needs and achieves other advantages by providing an apparatus and method for selecting at least one seed from a group of seeds. In general, the apparatus is configured for selecting at least one seed from a group of seeds contained in a seed container having a plurality of compartments, where each compartment is configured to hold a seed.

In some embodiments, the apparatus includes a seed receiving platform configured to receive the seed container, and an array of seed selectors, where each seed selector of the array of seed selectors is configured to expel a selected seed from a corresponding compartment of the seed container. The apparatus may further include a receptacle for collecting selected seeds expelled from the seed container and a transfer member configured to transfer each selected seed from the seed container to the receptacle. The array of seed selectors may be configured to automatically select at least one seed having a predetermined characteristic for transfer to the receptacle.

In some cases, the apparatus further includes a controller configured to receive a designation of seeds to be selected, wherein the designation is associated with the predetermined characteristic of the selected seed. The controller may be configured to actuate at least one seed selector to expel a selected seed from a corresponding compartment, and the controller may be configured to direct movement of the seed receiving platform to move the seed container into alignment with the array of seed selectors based on the designation of seeds to be selected to enable expulsion of the selected seeds.

The apparatus may also include a seed collecting platform configured to engage the receptacle. The receptacle may be a collection tray defining a plurality of cavities each configured to receive a selected seed, wherein the seed collecting platform is configured to receive an intermediate tray that is configured to hold the collection tray, and wherein the controller is configured to direct movement of the seed collecting platform to move the seed collecting platform into alignment with the transfer member to enable collection of each selected seed into a corresponding cavity of the collection tray. The apparatus may further include a processor, wherein the processor is configured to associate each selected seed with the corresponding cavity of the collection tray, and the receptacle may be an envelope.

In some cases, the apparatus may be configured to select seeds from more than one seed container and transfer the selected seeds to a single receptacle. The array of seed selectors may be configured to automatically select a plurality of seeds substantially simultaneously, or the array of seed selectors may be configured to automatically select a plurality of seeds in rapid succession. The apparatus may include at least one scanner configured to identify one or more of the seed container and the receptacle.

In other embodiments, a method of selecting one or more seeds from a group of seeds contained in a seed container having a plurality of compartments is provided, where each compartment is configured to hold a seed. The method may include receiving the seed container on a seed receiving platform, expelling a selected seed from a corresponding compartment of the seed container through actuation of one of an array of seed selectors, and automatically transferring each selected seed from the seed container to a receptacle, wherein each selected seed has a predetermined characteristic.

A designation of one or more seeds to be selected may be received, wherein the designation is associated with the predetermined characteristic. Also, the seed receiving platform may be moved such that the seed container is in alignment with the array of seed selectors based on the designation of seeds to be selected. In cases in which the receptacle is a collection tray, the step of automatically transferring may include moving the collection tray into alignment with a transfer member to enable collection of each selected seed into a corresponding cavity of the collection tray. More than one seed container may be received, and each selected seed may be automatically transferred from the seed containers to a single receptacle.

In some cases, the step of expelling a selected seed may include expelling the selected seed through contact with the seed container only. In addition, a plurality of seeds may be automatically expelled substantially simultaneously or in rapid succession.

Thus, the apparatus and method described in greater detail below allow for numerous seeds to be automatically selected substantially simultaneously or in rapid succession and re-configured in a short period of time and with limited user intervention.

BRIEF DESCRIPTION OF THE DRAWINGS

Figure 1:
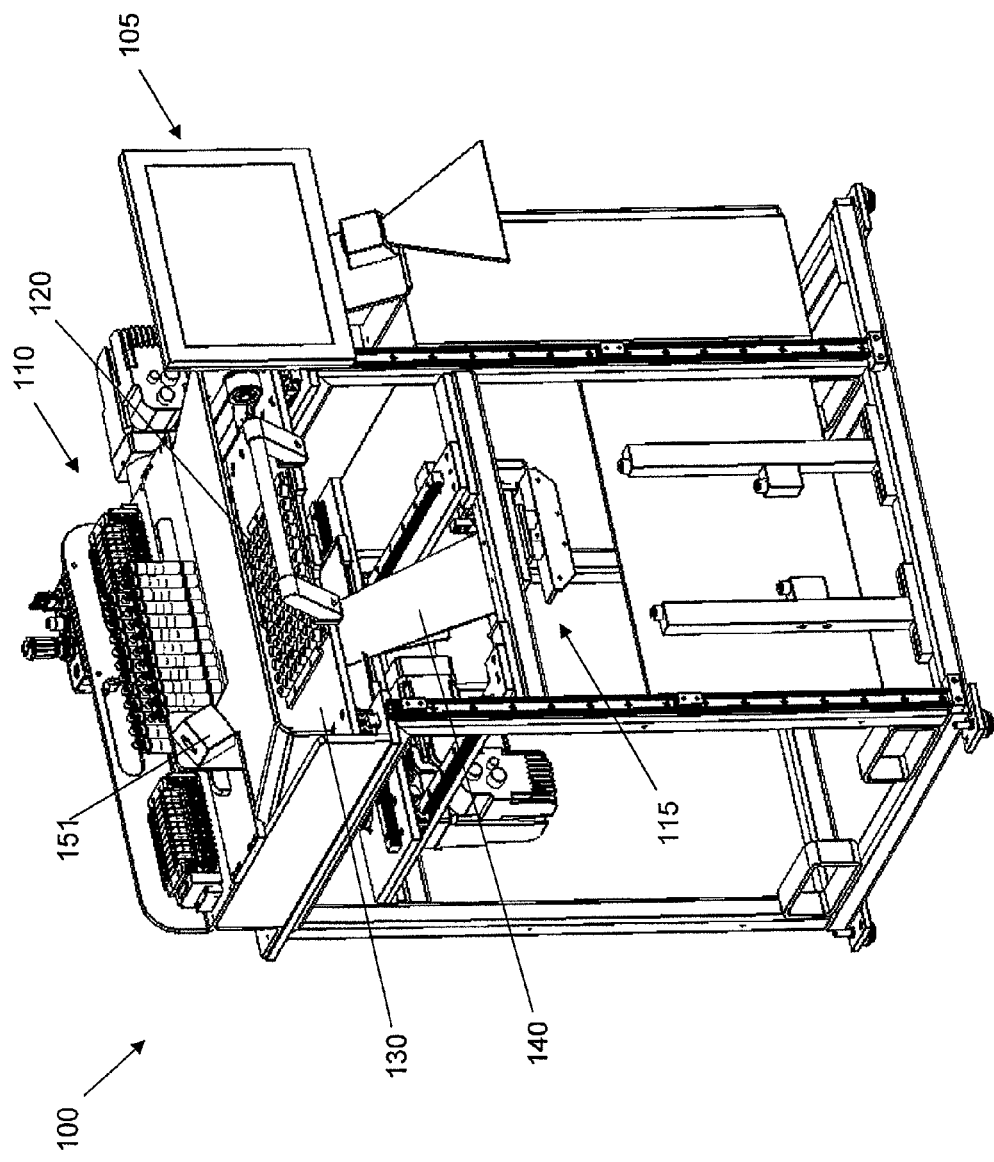
Figure 2A:
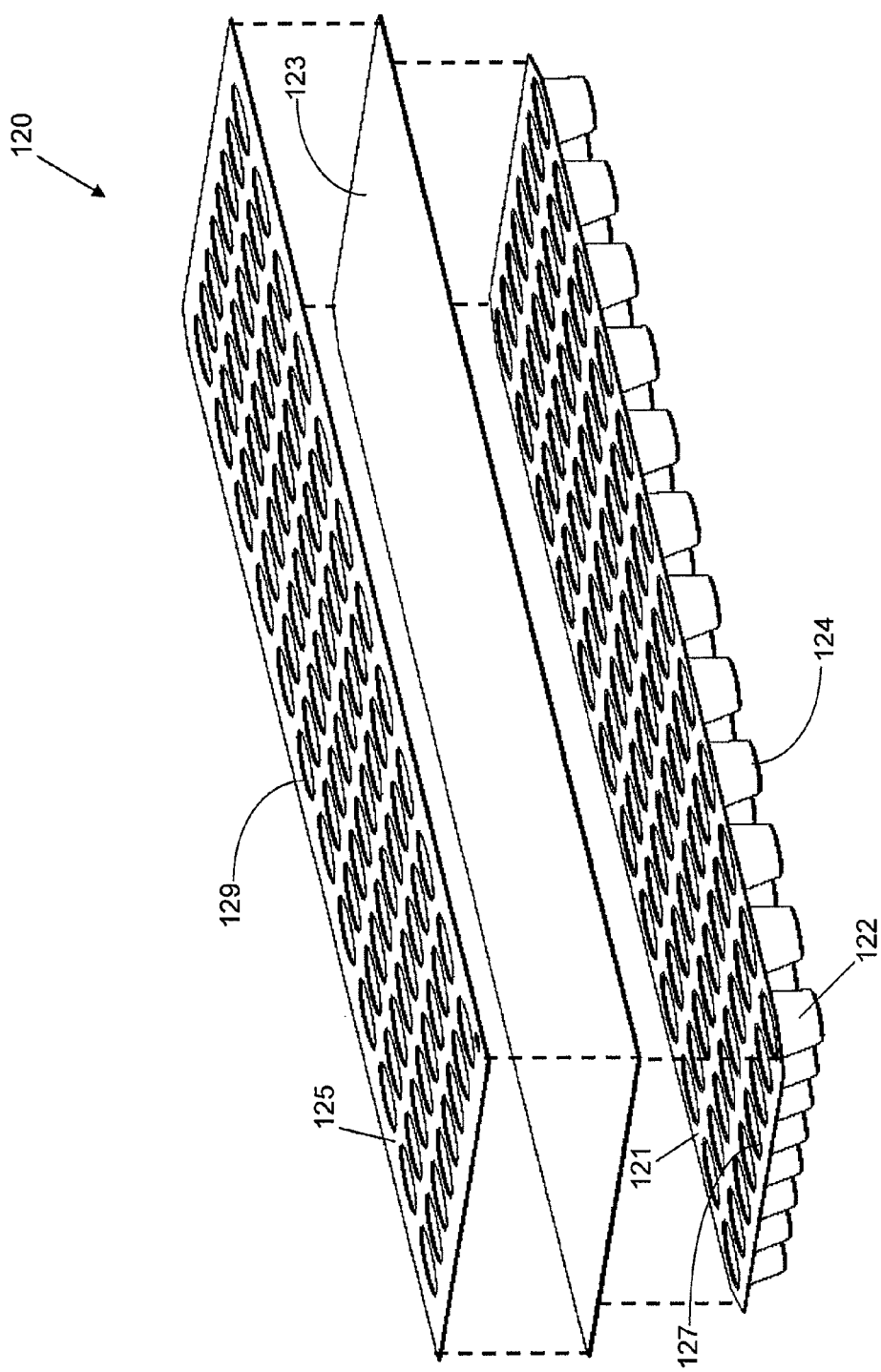
Figure 2B:
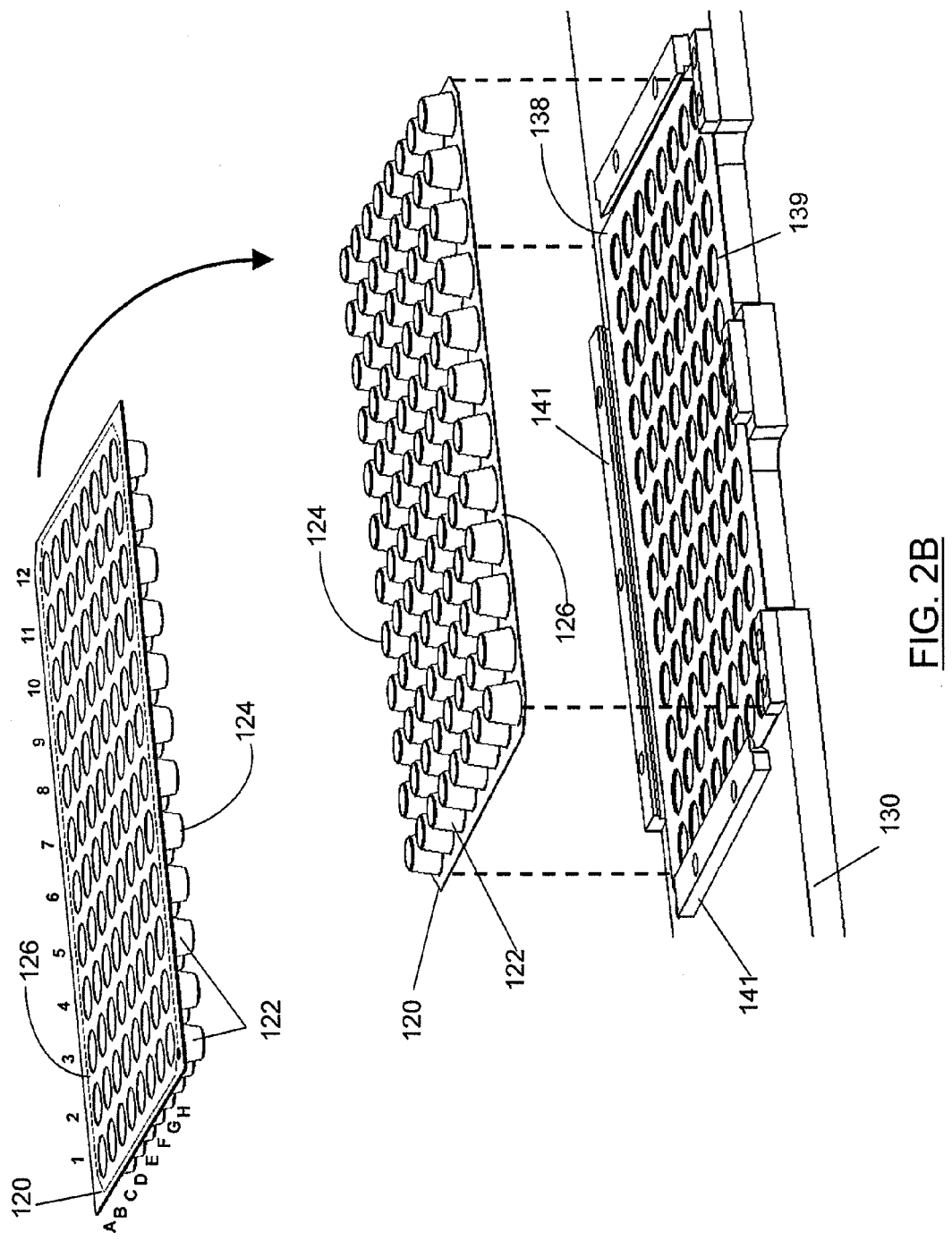
Figure 3:
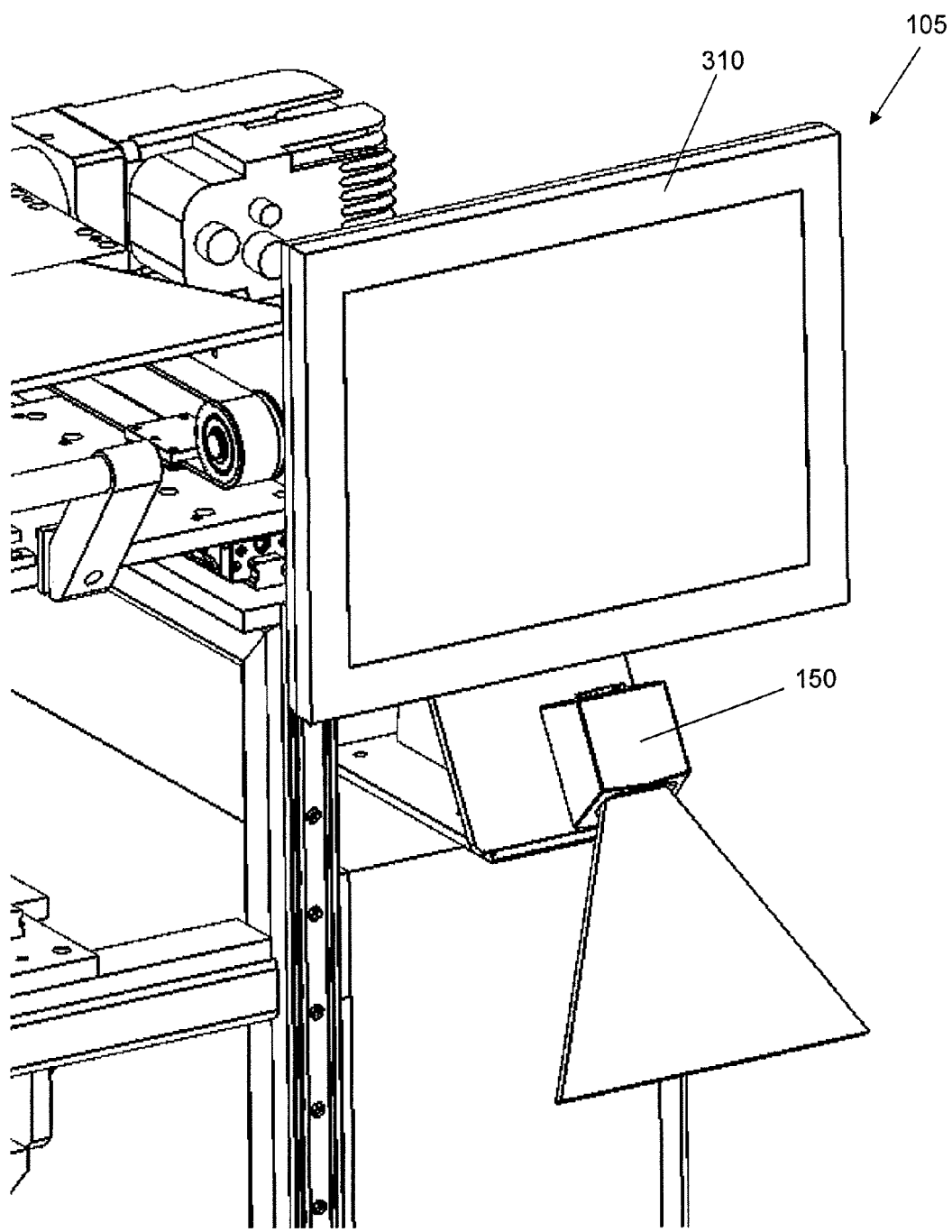
Figure 4:
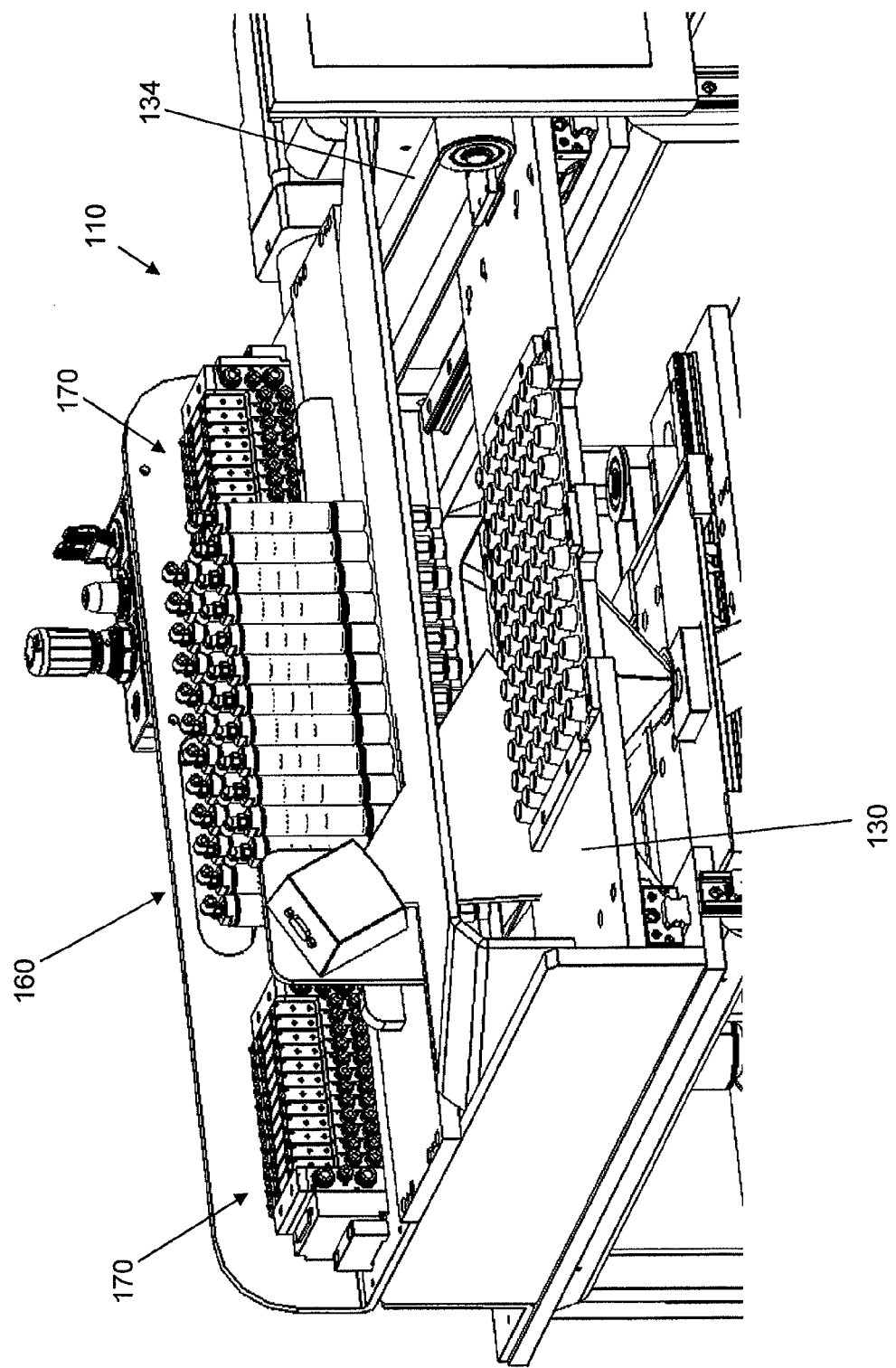
Figure 5:
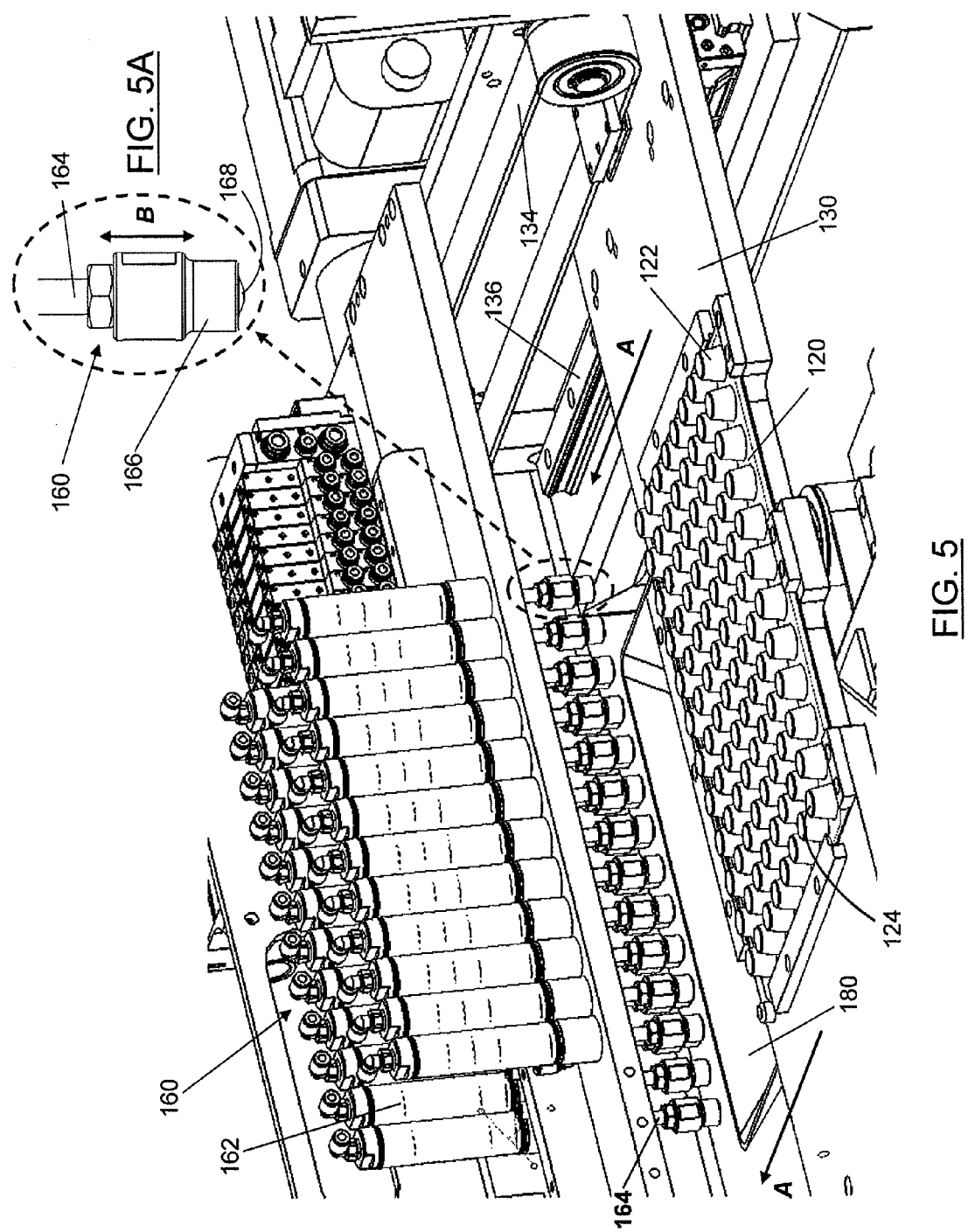
Figure 6:
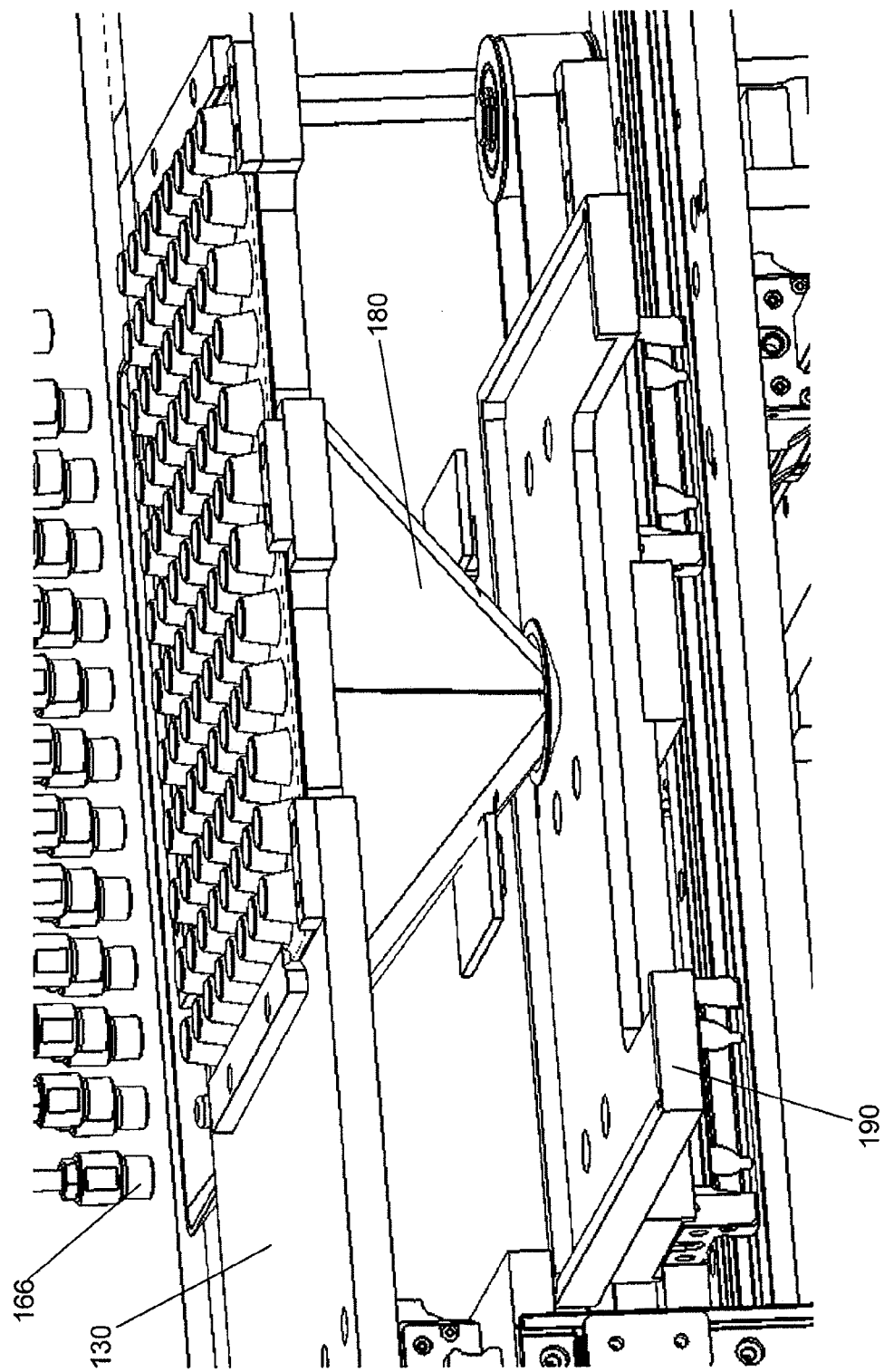
Figure 7:
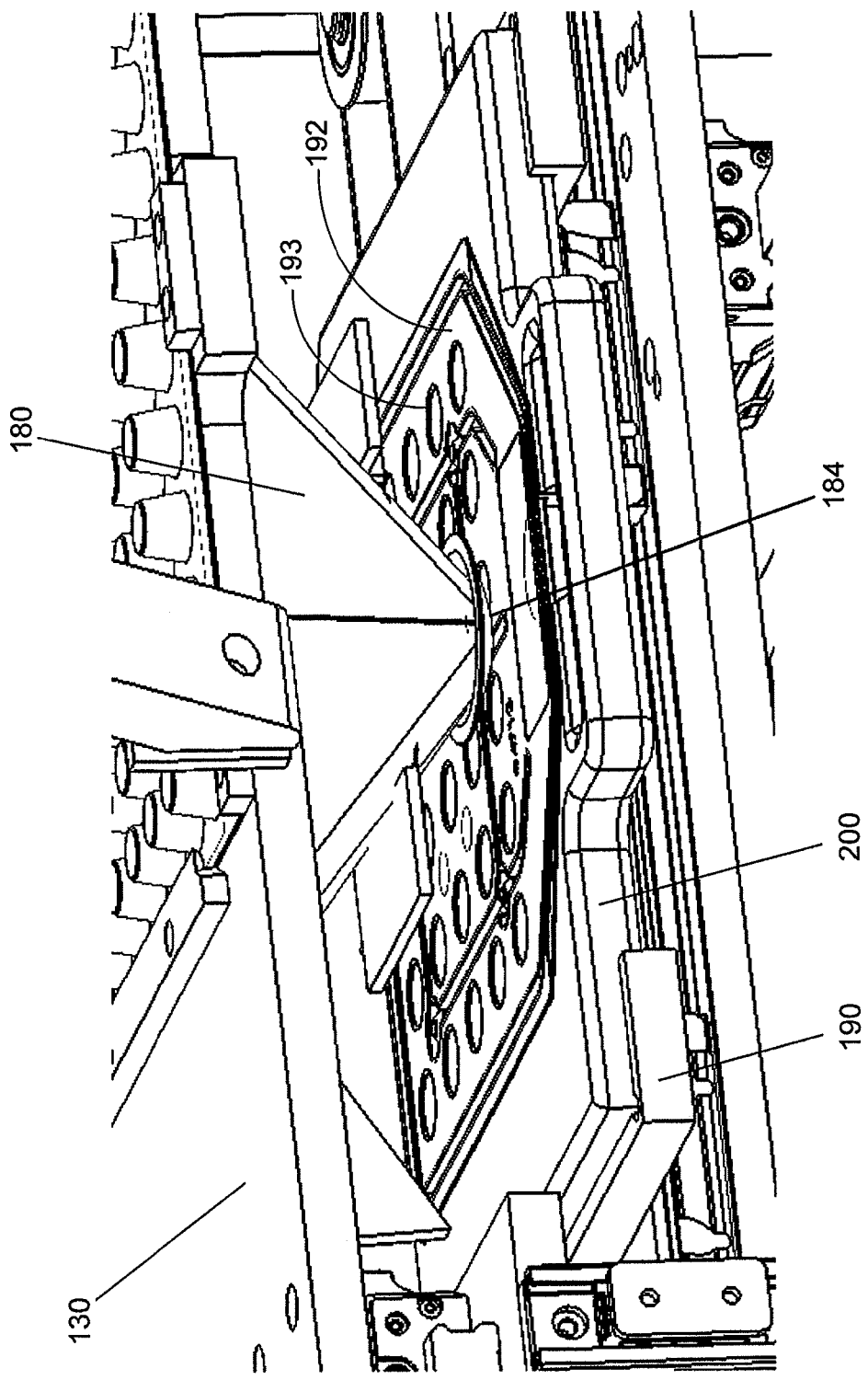
Figure 8:
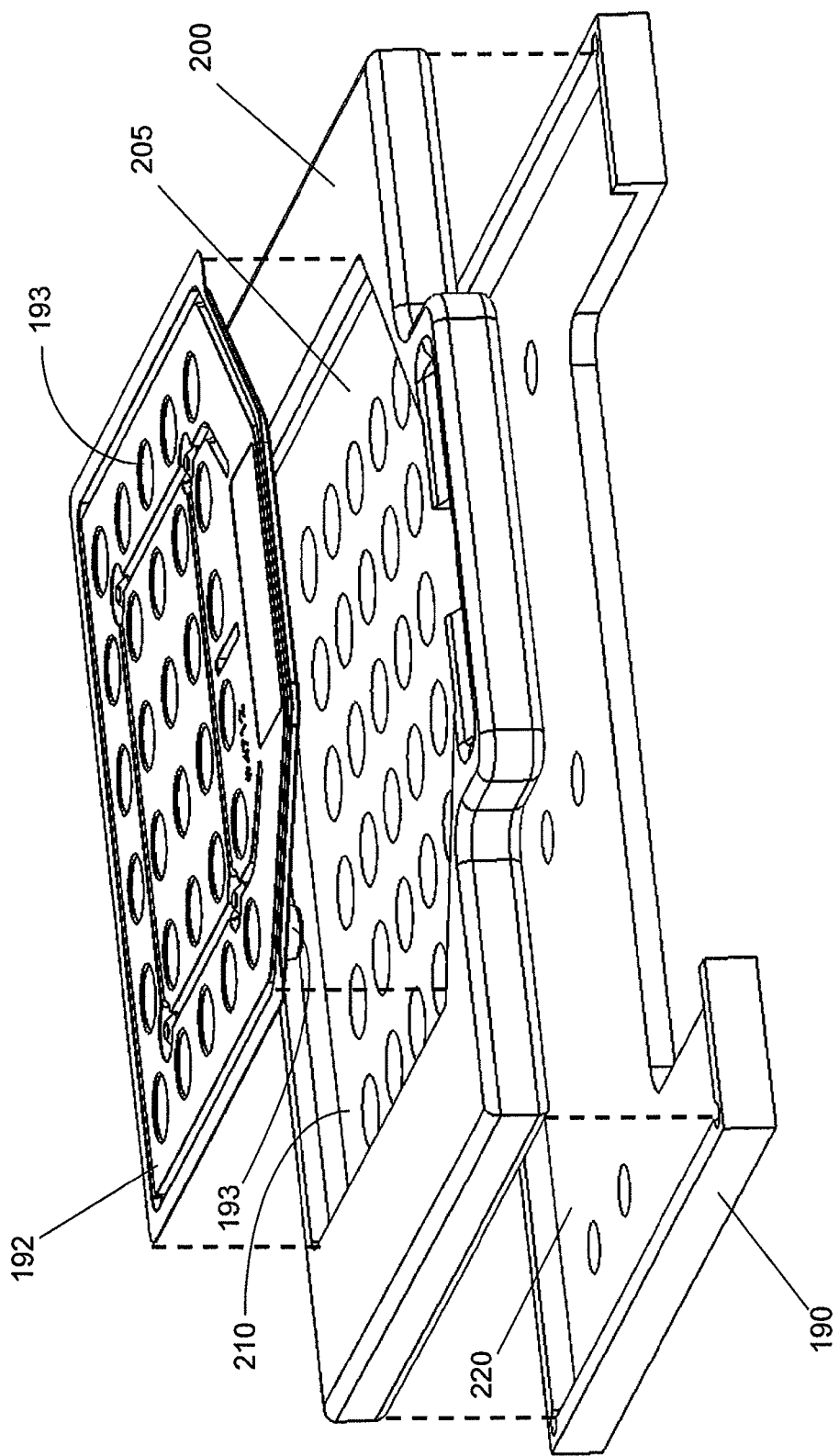
Figure 9:
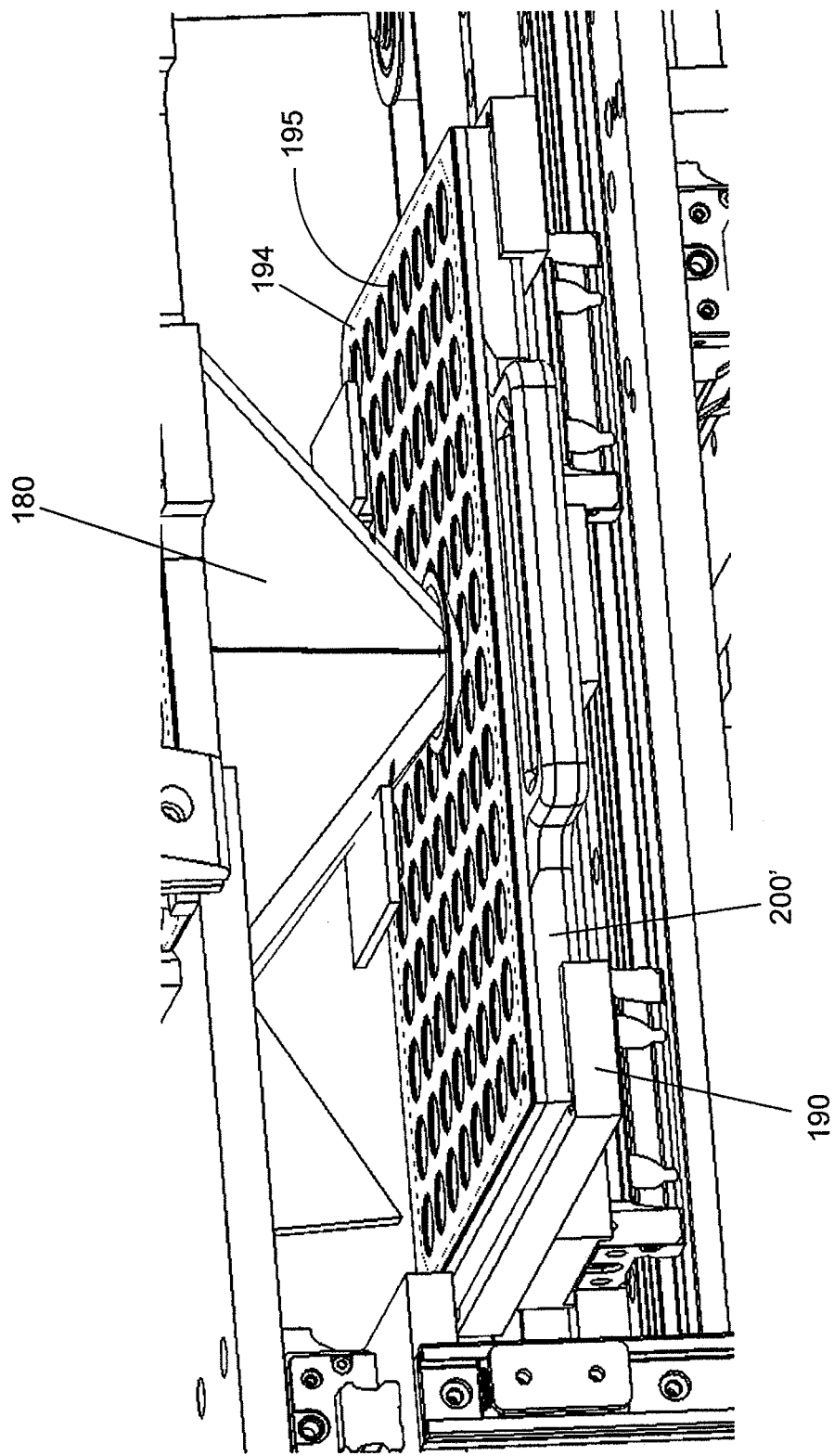
Figure 10:
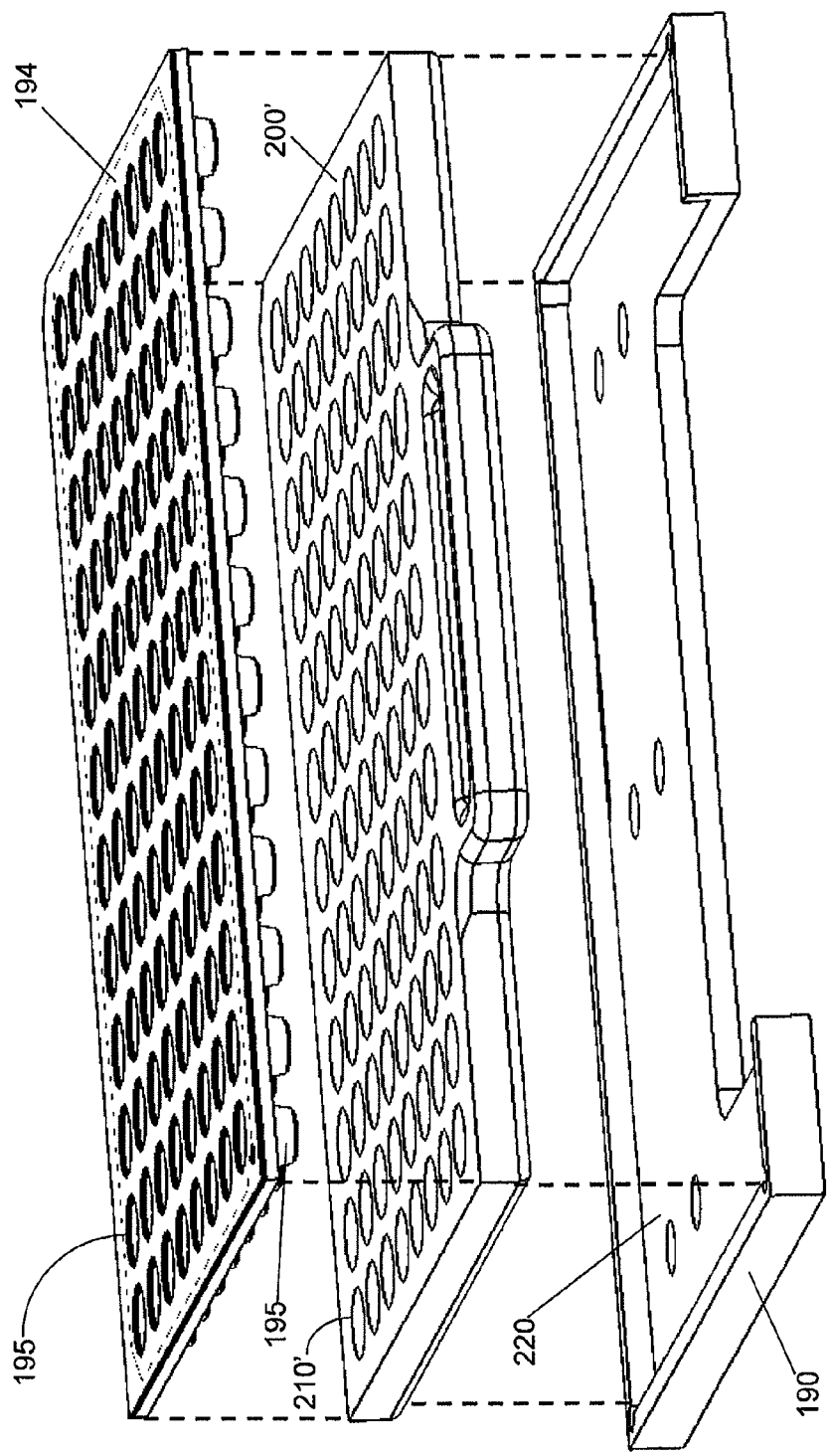
Figure 11:
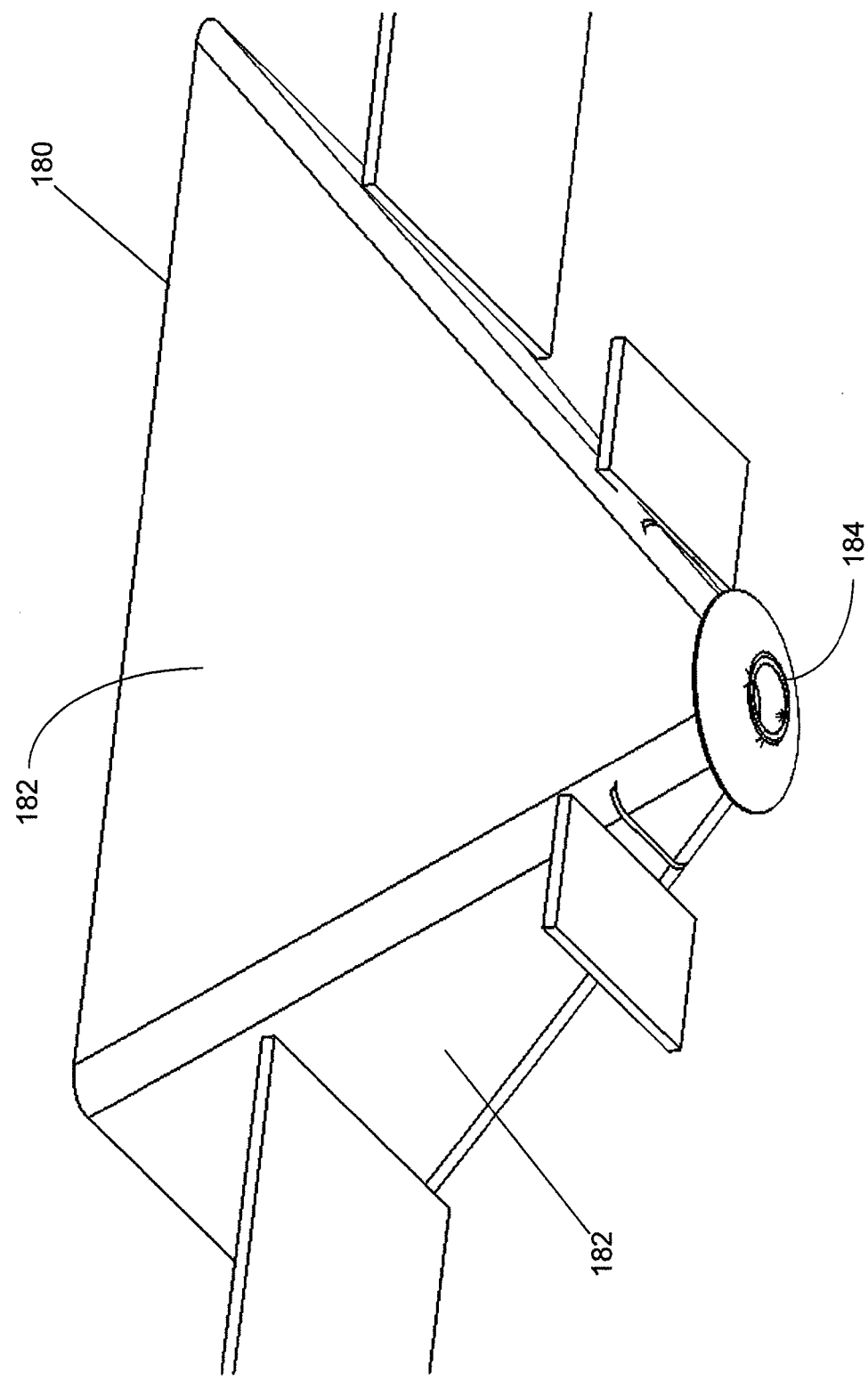
Figure 12:
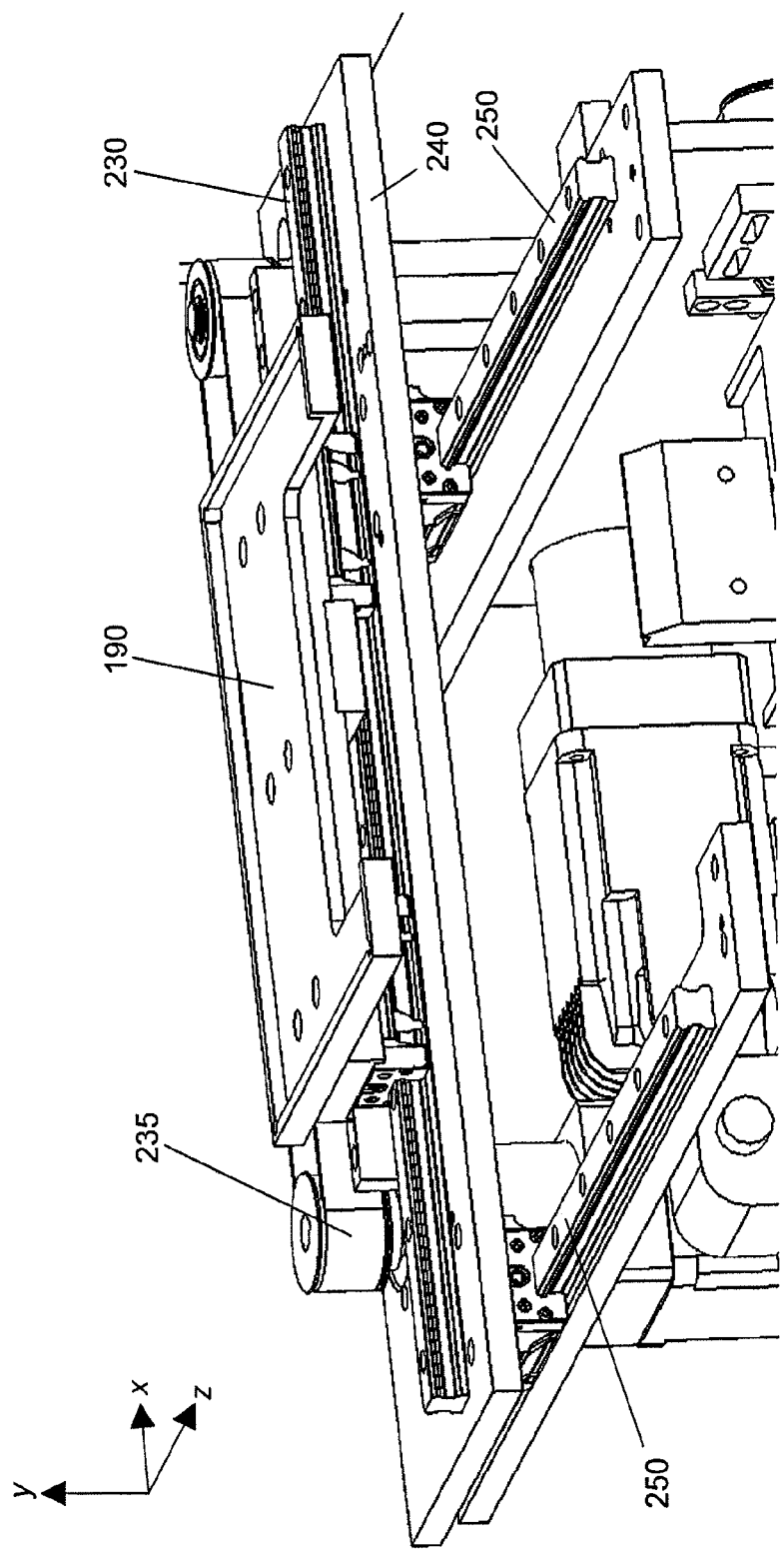
Figure 13:
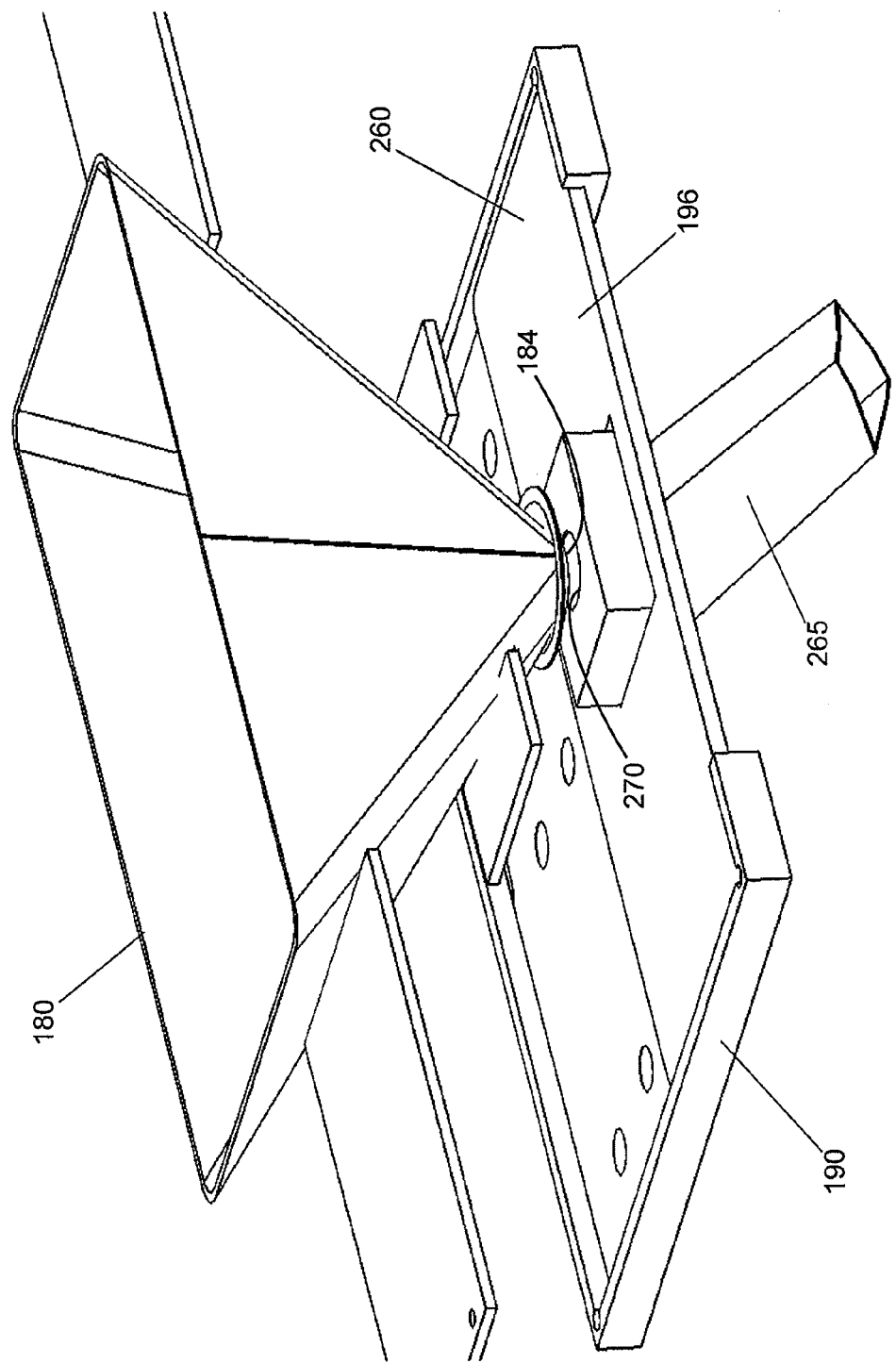
Figure 14:
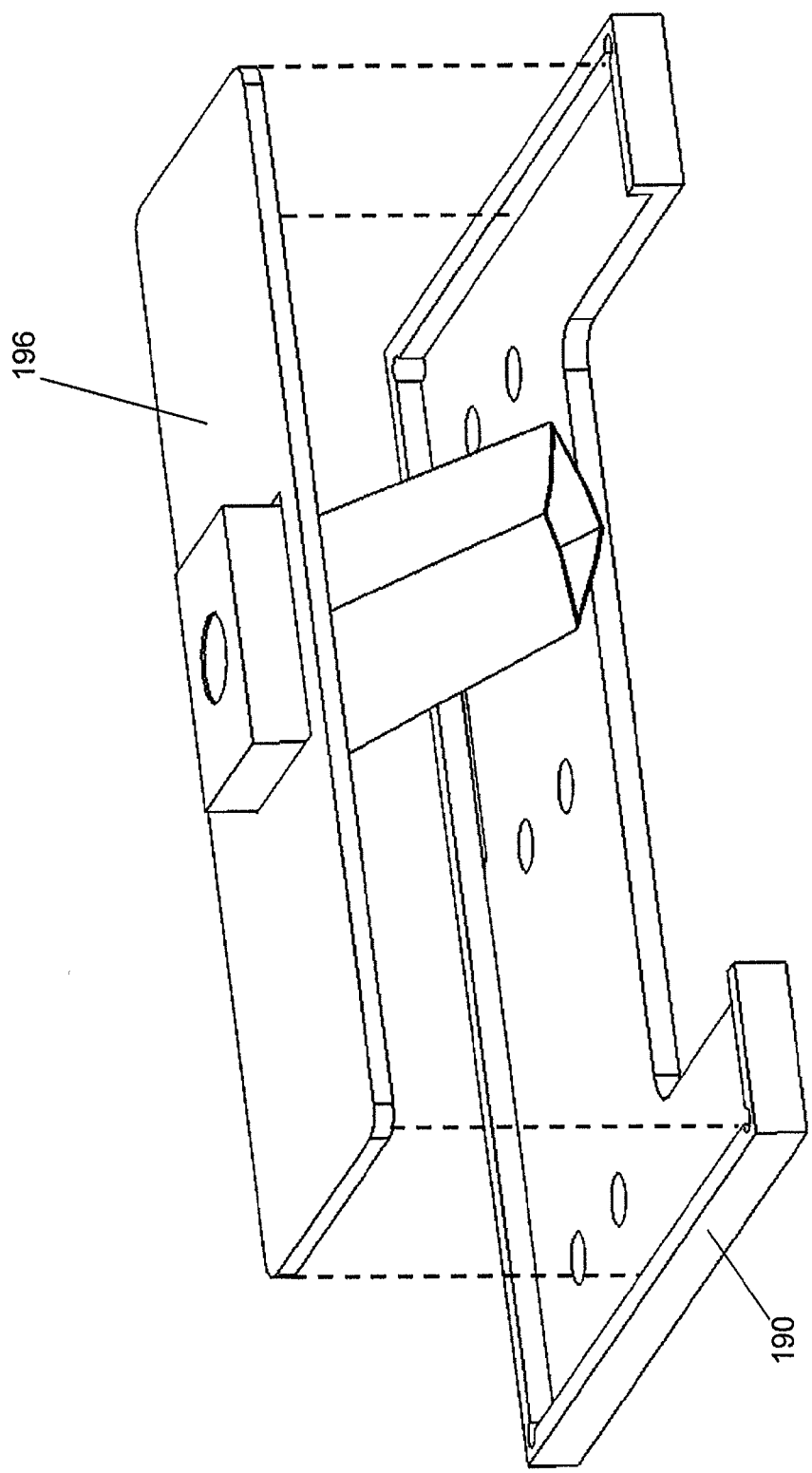
Figure 15:
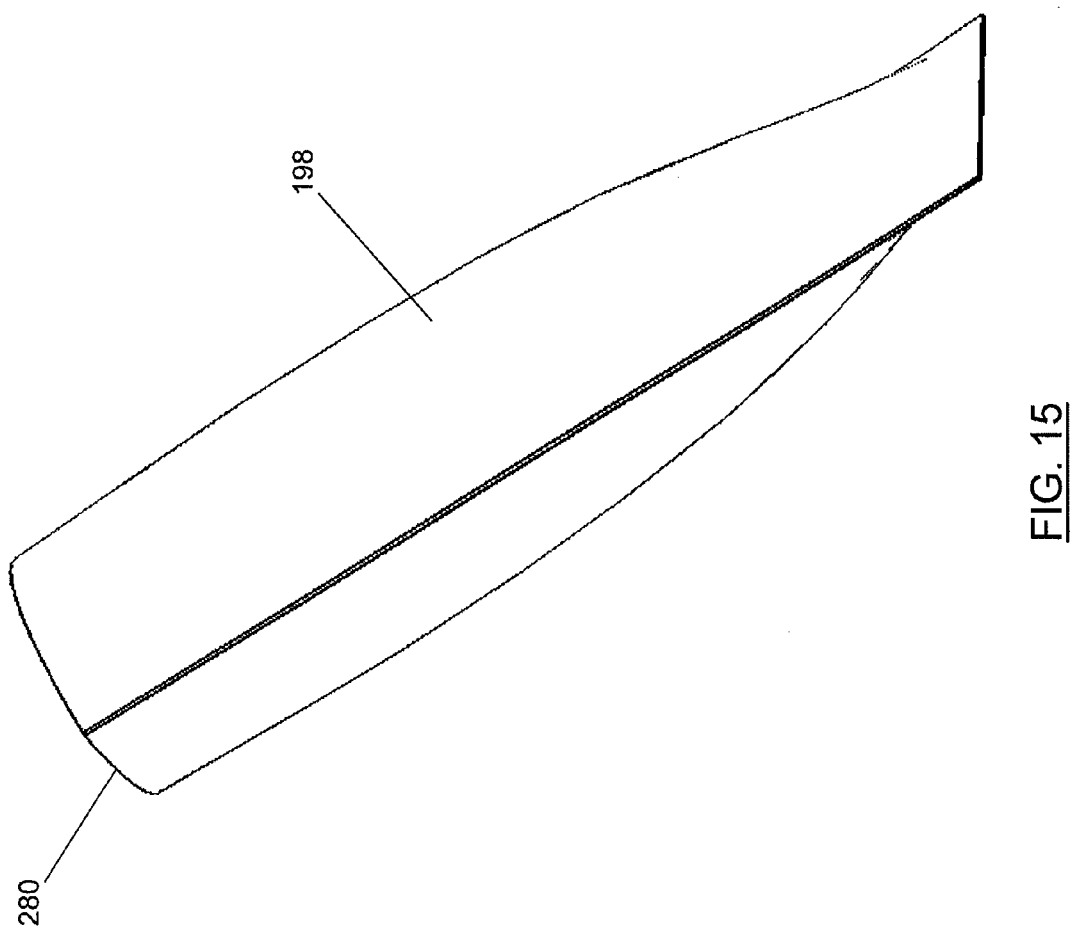
Figure 16:
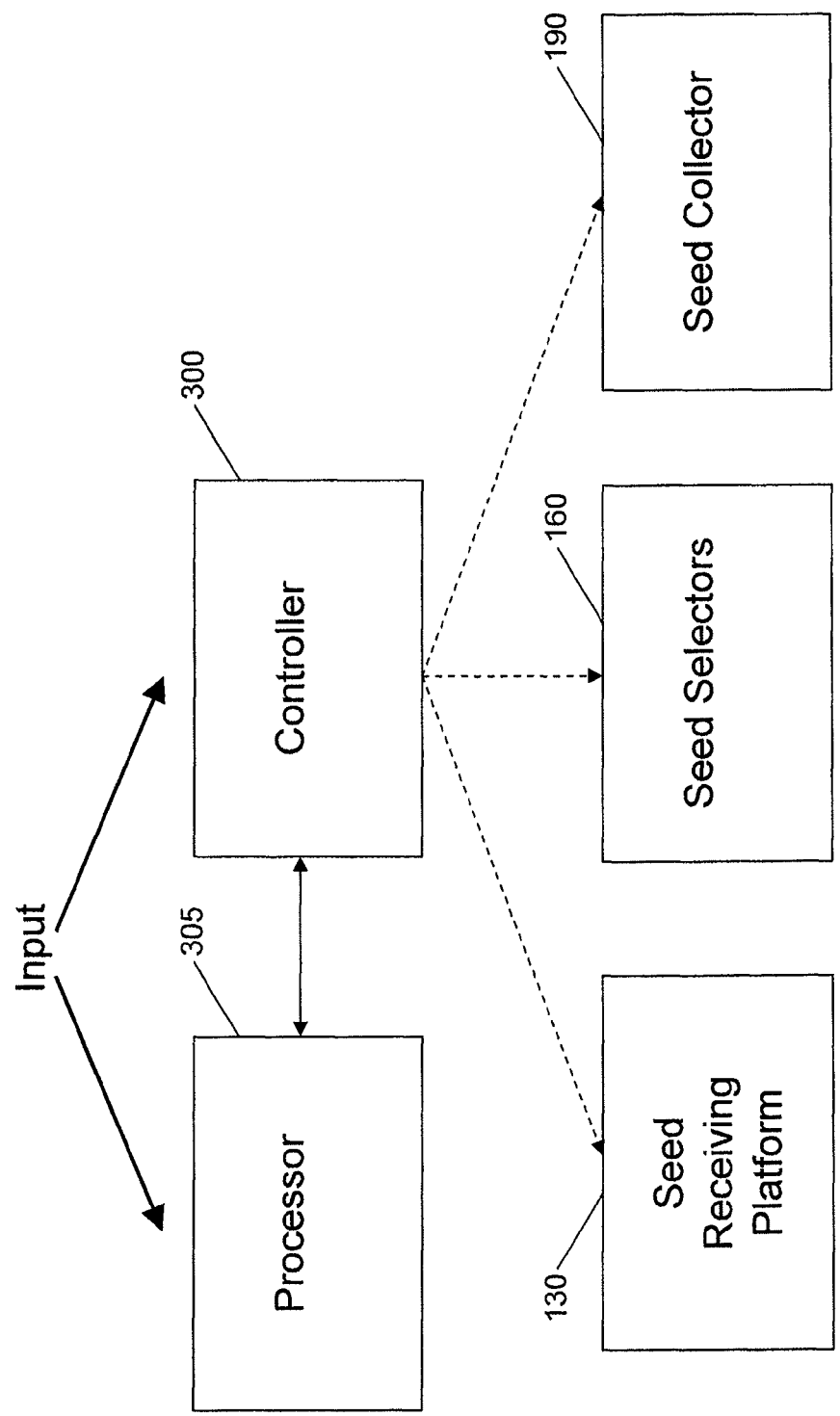

Having thus described the invention in general terms, reference will now be made to the accompanying drawings, which are not necessarily drawn to scale, and wherein:

FIG. 1 shows a perspective view of an apparatus configured to execute a method of selecting seeds from a group of seeds based on a predetermined characteristic in accordance with an exemplary embodiment of the present invention;

FIG. 2A shows an exploded perspective view of a seed container in accordance with an exemplary embodiment of the present invention;

FIG. 2B illustrates placement of the seed container of FIG. 2A onto a seed receiving platform in accordance with an exemplary embodiment of the present invention;

FIG. 3 shows a perspective view of a data input station in accordance with an exemplary embodiment of the present invention;

FIG. 4 shows a perspective view of a seed dispensing area in accordance with an exemplary embodiment of the present invention;

FIG. 5 shows a perspective view of an array of seed selectors of the seed dispensing area of FIG. 4;

FIG. 5A shows a detail perspective view of one of the seed selectors of FIG. 5;

FIG. 6 shows a perspective view of a transfer member and seed collecting platform in accordance with an exemplary embodiment of the present invention;

FIG. 7 shows a perspective view of the seed collecting platform of FIG. 6 with a 30-well collection tray installed in accordance with an exemplary embodiment of the present invention;

FIG. 8 shows an exploded perspective view of a seed collecting platform, intermediate tray, and 30-well collection tray in accordance with an exemplary embodiment of the present invention;

FIG. 9 shows a perspective view of the seed collecting platform of FIG. 6 with a 96-well collection tray installed in accordance with an exemplary embodiment of the present invention;

FIG. 10 shows an exploded perspective view of a seed collecting platform, intermediate tray, and 96-well collection tray in accordance with an exemplary embodiment of the present invention;

FIG. 11 shows a perspective view of a transfer member in accordance with an exemplary embodiment of the present invention;

FIG. 12 shows a perspective view of a seed collecting platform and corresponding mechanism for movement of the seed collecting platform in accordance with an exemplary embodiment of the present invention;

FIG. 13 shows a perspective view of a transfer member and seed collecting platform with funnel attachment installed in accordance with an exemplary embodiment of the present invention;

FIG. 14 shows an exploded perspective view of a seed collecting platform and funnel attachment in accordance with an exemplary embodiment of the present invention;

FIG. 15 shows a perspective view of an envelope receptacle in accordance with an exemplary embodiment of the present invention; and FIG. 16 shows a schematic illustration of a controller and components of the apparatus of FIG. 1 in accordance with an exemplary embodiment of the present invention.

DETAILED DESCRIPTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

As will be described below, the present invention is generally directed to an apparatus and method for selecting one or more seeds or seed portions from a group of seeds based on a predetermined characteristic of the selected seed. In various embodiments, the selected seeds are selected from multiple containers of seeds and re-configured into a single container for later use. For example, seeds may be selected from a container holding a number of seeds having a variety of characteristics (e.g., a characteristic relating to a biological trait, a genetic trait, a phenotypic trait, a morphological trait, or pedigree of the seed), where seeds having one particular characteristic are desired for selection. Based on previously acquired information associating each seed with one or more particular characteristics, seeds with the desired characteristic can be selected and packaged, for example, for planting or further testing.

As a result, embodiments of the present invention improve on the prior art by greatly reducing, and in some cases eliminating, the manual and time-intensive processes typically involved in selecting and re-packaging seeds. Additionally, embodiments of the present invention are scalable, and in some cases can be configured to automatically select and re-configure numerous seeds in a short period of time. Embodiments of the present invention may also track the re-configuration and re-packaging of the selected seeds, such that selected seeds are associated with the characteristic(s) used for their selection.

In this regard, seeds to be selected may typically be seeds that have been previously tested or analyzed to determine each seed's characteristics. In some cases, the tested seed is actually a portion of the original seed, as part of the seed may have been removed for analysis. The remaining portion, however, may be viable in that the remaining portion may be planted to yield a crop. Thus, the term "seed" as used herein will be understood to refer to both a whole seed and any portion of a seed, such as a portion of the seed remaining after analysis of the seed.

Although embodiments of the invention describe seeds, which may, for example, be corn, canola, soybean, rice, or any other seed of interest, one skilled in the art will recognize that the described apparatuses and methods may be used to select various other types of items from containers, such as parts, ingredients, compounds, medication, or the like.

Turning now to FIG. 1, an apparatus 100 for selecting one or more seeds from a group of seeds is shown. In general, the apparatus 100 includes a data input station 105, a seed dispensing area 110, and a seed collection area 115. Before the seed selection process commences, data is typically read from a seed container 120, such as the one shown in FIGS. 2A and 2B, and the seed container is placed on a seed receiving platform 130 in the dispensing area 110. Information regarding the selection criteria (e.g., a desired predetermined characteristic) is received by the apparatus 100 and used to determine which seeds to select. The selected seeds may then be expelled from the container and automatically transferred to a receptacle 140, such as an envelope (shown in FIG. 1), a 36-well tray, or a 90-well tray, as described in greater detail below.

Referring to FIG. 2A, the seed container 120 may comprise a first layer 121, a second layer 123, and a backing layer 125. The first layer 121 may define a plurality of compartments 122, with each compartment configured to hold a single seed (not visible) whose characteristic(s) have previously been determined. In the depicted embodiment, the plurality of compartments 122 have a truncated cone-like shape; however, in other embodiments the compartments could have any shape configured to isolate one or more seeds, including, but not limited to, various shapes typically used in "blister pack" applications, as well as other shapes, including domed oval and semi-spherical shapes, as well as circular, squared, oval, or rectangular wells. A truncated cone-like shape, such as the one depicted, may, for example, be preferable in cases in which it is desirable to expel the seed from the container as described below without destroying the container, as this particular shape lends itself to inverting easily.

In various embodiments, the first layer 121 of the seed container 120 may be made of a rigid, semi-rigid, or non-rigid material, which, in some embodiments, may be at least partially transparent. For example, various plastics may be suitable materials for the first layer 121, such as thermoplastics including, but not limited to, acrylonitrile butadiene styrene (ABS), acrylic, polyvinyl chloride(s) (PVC) with or without plasticizers such as phthalates, polyethylene, and polystyrene as well as many commercially available and possibly trademarked materials for purchase from Professional Plastics, 1810 E. Valencia Drive, Fullerton, Calif., 92831. In the depicted embodiment, the first layer 121 is made of a semi-rigid transparent thermoplastic PVC material.

In the depicted embodiment, the second layer 123 may be provided to seal or otherwise maintain the seed within its respective compartment 122. For example, the second layer 123 of seed container 120 may be configured to be affixed to the first layer 121 so as to cover the openings 127 of the compartments 122 and thus close off the compartments formed by the first layer 121. The degree of closure may vary depending on the requirements of the application. In some embodiments, the second layer 123 could close off each compartment 122 such that seeds contained in each compartment are partially confined, or, as in the depicted embodiment, fully confined such that one or more of a range of contaminants are substantially prevented from entering one or more of the compartments. Contaminants could include, air, water, light, radiation, insects, fungus, protozoa, monera, gasses, viruses, elements, compounds, or any other contaminant deemed to affect the quality of the seeds. Additionally, by fully confining each seed, the second layer 123 may help to prevent cross-contamination between seeds held in different compartments 122.

In various embodiments, the second layer 123 of the seed container 120 may be made out of various materials, including, but not limited to, plastic materials, foil materials, paper (s), non-woven fibers, bio-plastics, and/or starch and starch-based materials. In the depicted embodiment, the second layer 123 is made of a ruptureable foil material such that upon application of force, the second layer may be ruptured to release the contents of the compartment 122. In various embodiments, the second layer 123 may optionally include or have applied to it one or more additional layers of the same or a different type of material, and thus in various embodiments the second layer may comprise a combination of layers. Thus in some cases, the second layer 123 may include the backing layer 125 described below.

In some embodiments, the second layer 123 may be affixed to the first layer 121 using an adhesive, such as a heat activated adhesive, or other binding agents or materials such as clips, pins, staples, rivets, brads, tape, cellophane, shrink wraps, wax, or other materials or combinations thereof. In some cases, such as the one depicted in FIG. 2A, the second layer 123 is held to the first layer 121 using a backing layer 125. The backing layer 125 may be made of materials similar to the first layer 121 and may be provided to add stiffness or strength to the container 120. For example, in the depicted embodiment, the backing layer 125 is made of cardboard.

The backing layer 125 may be applied to the first and second layers 121, 123 such that the backing layer partially wraps around the edges of the first and/or second layers and thereby holds the second layer to the first layer. Thus, the backing layer 125 may define openings 129 corresponding to the openings of the compartments 122 formed in the first layer 121, such that the backing layer does not impede access to the compartments 122 through the second layer 123.

The seed container 120 may also have physical characteristics which may aid in identifying portions and/or the desired orientation of the first layer 121. For example, the first layer 121 may include one or more beveled corners, which may identify a specific corner of the seed container 120 for orientation purposes. Although the seed container 120 is shown with beveled or notched corners, it should be appreciated that in other embodiments one or more, or all, of the corners may not include notches or bevels.

Each compartment 122 of the seed container 120 may be configured to hold a single seed (not visible) whose characteristic(s) have previously been determined. By associating the location of each compartment 122 with the predetermined characteristic of the seed, a user may thus select seeds with a particular characteristic by expelling seeds from the compartments associated with the desired characteristic. For example, in the case of a 96-compartment seed container having an 8×12 array of compartments 122, as shown, the compartments may be indexed such that seeds may be designated by identifying particular compartments using the indexing system. In the example shown in FIG. 2B, the compartment 122 in the second row from the front, third column from the left, may have an index of G3. Each compartment 122 may be similarly indexed. Thus, each index (A1 through H12) may be associated with a predetermined characteristic and may be used to designate the seed contained therein. It should be noted that although the depicted embodiment shows a 96-compartment seed container, in various embodiments the apparatus and method of the present invention may utilize seed containers of various sizes and shapes, and those having a variety of numbers of compartments.

The information associating each compartment 122 with the corresponding predetermined characteristic may be coded onto the container itself or a tag on the container, such as with a Universal Product Code (UPC) label, radio frequency identification (RFID) tag, or other readable tag to allow the information to be accessed by the apparatus 100. Thus, as shown in FIG. 3, the data input station 105 of the apparatus 100 may in some cases include a scanner 150 or other tag reader for reading the information from the container 120. For example, a user may pass the container 120, or more specifically the tag on the container, under the scanner 150 to allow the apparatus 100 to access the information associating each compartment 122 with the predetermined characteristics. In this way, upon receiving further information from the user regarding the desired characteristic, the apparatus 100 is able to determine which seeds to select by determining which compartments carry seeds having the desired characteristic, as described in greater detail below.

Once the seed container 120 has been identified, such as via the scanner 150 as described above, the container may be loaded into the seed dispensing area 110. Referring to FIG. 4, the seed dispensing area 110 may include a seed receiving platform 130 configured to receive the seed container 120, an array of seed selectors 160, and a mechanism for actuating the seed selectors, such as a bank of solenoid valves 170. The seed receiving platform 130 may be movable between a loading position (withdrawn, as depicted) and an operating position (retracted, not shown) and may include belts 134 and tracks 136 in conjunction with one or more motors to allow the user to move the seed receiving platform between positions.

Turning to FIGS. 2B and 4, a user may load the seed container 120 into the seed dispensing area 110 by first moving the seed receiving platform 130 from the operating position to the loading position. This may be done manually by the user or automatically, such as through the use of the belts 134 at the start of a selection operation, as described below. In some cases, the seed receiving platform 130 may be enclosed within the apparatus and may be accessible using a door (not shown) for safety purposes, in which case the user would first have to open the door to load or unload a seed container 120.

Once in the loading position, the seed container 120 is placed upside down (i.e., with the backing layer 125 contacting the seed receiving platform 130 and the first layer 121 of each compartment extending away from the platform) within a recess 138 or other area of the platform configured to correspond to the shape of the seed container. The recess 138 may thus include portals 139 corresponding to the compartments 122 of the seed container 120 that provide an opening for the seed in each compartment to pass through the seed receiving platform 130 when the seed is expelled.

To secure the seed container 120 in position about the recess 138, stays 141 may be provided at intervals around the perimeter of the recess 138. The stays 141 may be permanently fixed to the platform 130, and the seed container 120 may be slid into engagement with the stays to hold the container in position. Alternatively, the stays 141 may be movable between a secured position and an unsecured position or may be fastened to the platform 130 (e.g., using screws) once the container 120 is in place to secure the container.

As shown in FIG. 5, in which some components have been removed for clarity and ease of explanation, the seed receiving platform 130 may be configured to move the seed container 120 into alignment with the array of seed selectors 160, such as via an arrangement of belts 134 that draw the seed receiving platform back and forth (as depicted by the arrows A) along one or more tracks 136. For example, the array of seed selectors 160 may include two rows of twelve individual selectors that are positioned to correspond with two of the rows of compartments 122 of the seed container 120, such that as the seed receiving platform 130 moves under the seed selectors, the seed in each compartment can be selectively accessed.

In this regard, each seed selector 160 may be configured to expel a selected seed from a corresponding compartment 122 of the seed container 120. As shown in FIGS. 5 and 5A, each seed selector 160 may include a cylinder 162 within which a shaft 164 is configured to slide. For example, each seed selector 160 may be pneumatically actuated (e.g., by compressed air that is introduced or evacuated from the cylinder 162 through the action of the bank of solenoid valves 170) such that the piston 164 is moved toward the corresponding compartment 122 of the seed container 120, shown by the arrow B in FIG. 5A. An expulsion head 166 may be formed or attached to the end of the piston 164. The head 166 may be configured to contact the base 124 of a compartment 122 positioned below the head and to expel the seed contained therein through the second layer 123 of the compartment. The expulsion head 166 may thus include a rounded tip 168 configured to contact the seed through the base 124 upon engagement and thereby urge the seed out of the compartment 122 through the second layer 123. The force of the head 166 acting on the seed through the base 124 may, in other words, create a tear or opening in the second layer 123, through which the selected seed is urged to pass. Thus, the selected seeds may be expelled through contact with the seed container only (e.g., without direct contact between the expulsion head 166 and the seed itself).

Referring to FIGS. 6-15, once a selected seed has been expelled from its respective compartment 122, the seed passes through a transfer member 180 and is directed towards a seed collecting platform 190. In turn, the seed collecting platform 190 is configured to receive a number of attachments that can have different configurations, as described below, for collecting the selected seeds that are expelled from the seed container 120 in different kinds of receptacles.

In FIG. 6, the seed collecting platform 190 is shown without any attachments or receptacles. As depicted, the seed collecting platform 190 may be a movable platform that is configured to receive different types of receptacles for collecting the selected seeds. In FIG. 7, for example, the seed collecting platform 190 is shown with a 30-well collection tray 192 in place. In FIG. 9, the seed collecting platform 190 is shown receiving a 96-well collection tray 194. In FIG. 13, the seed collecting platform 190 is shown with a funnel attachment 196 in place, the funnel attachment being configured to engage an envelope 198 (shown in FIG. 15) for collecting the selected seeds. Other types and sizes of receptacles may also be used, with corresponding attachments to allow the particular receptacle to engage the seed collecting platform, if necessary.

For example, turning to FIGS. 7 and 8, which show the seed collecting platform 190 receiving a 30-well collection tray 192, an intermediate tray 200 may be provided to adapt the 30-well collection tray for fitting into the seed collecting platform. The intermediate tray 200 may thus include a recessed portion 205 configured to match the shape and depth of the 30-well collection tray 192, such that the collection tray is able to fit into the recessed portion in a secure manner. The recessed portion 205 may further include indentations 210 that are substantially aligned with the plurality of cavities 193 defined by the collection tray 192. In this way, the engagement of each cavity 193 or "well" of the collection tray 192 with a corresponding indentation 210 may further enhance the stability and fit of the collection tray in the intermediate tray 200. The intermediate tray 200 is, in turn, configured to fit into a recessed portion 220 of the seed collecting platform 190, as shown in FIG. 7.

Similarly, with reference to FIGS. 9 and 10, a 96-well collection tray 194 may be received in the seed collecting platform 190 through the use of a different intermediate tray 200', which is configured to both receive the 96-well collection tray and be received in the recessed portion 220 of the seed collecting platform. Thus, as described above, the intermediate tray 200' similarly defines indentations 210' that are substantially aligned with the plurality of cavities 195 of the collection tray 194 so that the collection tray can be held in place by the intermediate tray. The intermediate tray 200' and collection tray 194, in turn, fit into and are held by the seed collecting platform 190, as shown in FIG. 9.

Referring again to FIGS. 7 and 9, once the collection tray 192, 194 is in place in the seed collecting platform 190 using the appropriate intermediate tray 200, 200', the collection tray can be positioned to receive selected seeds into the corresponding cavities 193, 195. Thus, in some embodiments, the seed collecting platform 190 is configured to move with respect to the transfer member 180 to position a particular cavity 193, 195 in alignment with the transfer member to receive a particular expelled seed, as will be described in greater detail below.

In this regard, the transfer member 180 may be positioned between the seed receiving platform 130 and the seed collecting platform 190, as shown, for example, in FIG. 7. The transfer member 180, which is depicted in FIG. 11, may be configured to span the distance between the columns and rows of expulsion heads 166 such that seeds expelled by any of the heads from the corresponding compartments 122 will be caught by the transfer member and directed towards the seed collecting platform 190, as best seen in FIG. 5. Thus, the transfer member 180 may have one or more sloped walls 182 that are configured to direct the expelled seeds towards an opening 184 for depositing the selected seed into a particular compartment 122, regardless of which expulsion head 166 expelled the seed.

In the embodiments shown in FIGS. 7 and 9, which include a collection tray 192, 194 having a plurality of cavities 193, 195, a selected seed may be directed into a particular cavity by moving the seed collecting platform 190 to various positions with respect to the opening 184, and mentioned above. In this way, the apparatus can place each selected seed into a particular cavity 193, 195 by moving the seed collecting platform 190 such that the desired cavity is aligned with the opening 184 to receive the seed coming out of the opening.

Turning now to FIG. 12, in which various components have been removed for ease of explanation, the seed collecting platform 190 may be configured to move in the x- and z-directions via one or more motors, belts, tracks, and/or movable platforms. For example, in the depicted embodiment, the seed collecting platform 190 is configured to be driven along a first track 230 by a belt 235 in the x-direction. The first track 230 may be disposed on a platform 240 which is itself movable along one or more second tracks 250 in the z-direction. Thus, the combination of movement in the x-direction along the first track 230 and in the z-direction along the second tracks 250 via the platform 240 allows the seed collecting platform 190 to have a range of motion such that any one of the cavities 193, 195 of the collection trays 192, 194 may be placed in position to receive seeds expelled from the opening 184 of the transfer member 180.

In other embodiments, not shown, however, the seed collecting platform 190 may be stationary, and the transfer member 180 may be configured to move to position selected seeds in particular cavities 193, 194. In still other embodiments, neither the transfer member 180 nor the seed collecting platform 190 may be required to move. For example, turning to FIGS. 13-15, in some embodiments it may not be important to place selected seeds in individual cavities of a collection tray. Rather, all selected seeds may be collected in a bulk container, such as an envelope 198, shown in FIG. 15.

In this regard, a funnel attachment 196 may be used to adapt the seed collecting platform 190 for collecting seeds in an envelope 198. The funnel attachment 196 may include a tray portion 260 and a chute 265 extending from the tray portion. The tray portion 260 may be configured to be received in the recessed portion 220 of the seed collecting platform 190, as shown in FIG. 13.

The tray portion 260 may further define an inlet opening 270 configured to receive selected seeds from the opening 184 of the transfer member, and the chute 265 may define an outlet opening 275 configured to engage and deposit seeds into the envelope 198. A pathway may thus be defined between the inlet opening 270 and the outlet opening 275, such that selected seeds enter the funnel attachment 196 through the inlet opening 270, travel through the chute 265, and exit the chute through the outlet opening 275 to be collected by the envelope 198. In this regard, an open end 280 of the envelope 198 may be configured to attach to or around, or otherwise engage, the chute 265 proximate the outlet opening 275, such as via fasteners, adhesive, a mechanical fit (e.g., based on the configuration and/or material of the envelope with respect to that of the chute), or other method of attachment. Once the selected seeds have been collected in the envelope 198, the envelope may be removed from the funnel attachment 196 and sealed for future handling.

Accordingly, a user may operate the apparatus to select one or more seeds from a group of seeds and either re-configure the selected seeds into a collection tray or collect the selected seeds in an envelope or other receptacle for future handling and/or use.

Turning to FIGS. 1, 3, and 16, a user may first prepare the apparatus for the seed selecting operation by providing inputs regarding a designation of the seed or seeds to be selected, the desired characteristics of the seeds, the seed container(s) from which the seeds are to be selected, the receptacle(s) in which the seeds are to be collected, and/or various other parameters. In this regard, the apparatus 100 may include a programmable logic controller 300 and/or a processor 305, such as an onboard personal computer (PC), shown in FIG. 16, that run the operation of the apparatus.

The inputs may be provided to the controller 300 and/or the processor 305 in various ways. For example, the inputs may be set up prior to running the operation and may be stored in software accessible to the controller 300 and/or the processor 305. Thus, the user may select a set of inputs (e.g., a "job") from a list of stored jobs displayed on a display 310, shown in FIG. 3. The display 310 may, for example, be a touch screen display, and the user may select the desired job by touching the screen. Alternatively, a keyboard and/or mouse may be provided to facilitate the user's interaction with the apparatus.

Once the job is selected, the user may scan a barcode or other machine-readable tag on the seed container 120 using the scanner 150. By scanning the seed container 120, the processor 305 may determine which compartments 122 of the scanned seed container 120 hold the seeds having the predetermined characteristics, as dictated by the chosen job. In this way, the seeds possessing the predetermined characteristics may be selected by expelling those particular seeds from the corresponding compartments 122.

The scanned seed container 120 would then be placed by the user onto the seed receiving platform 130 by moving the seed receiving platform to the loading position, turning the seed container "upside down," and placing it in the recess 138 of the platform, as shown in FIG. 2B and described above. The user would then move the seed receiving platform 130 to the operating position, where the seed selectors 160 can access the various compartments 122 of the seed container 120. In some cases, the apparatus 100 includes a second scanner 151 positioned in the dispensing area 110, such that the second scanner is able to read the bar code or tag of the seed container 120 with the seed container in place on the seed receiving platform 130, rather than requiring the seed container to be manually scanned prior to installation. In still other cases, the second scanner 151 may confirm that the correct seed container 120 has been placed on the seed receiving platform 130 and/or that the seed container is properly installed.

The user may then install the receptacle 140 that will be used to collect the selected seeds. As discussed above, the receptacle may be a collection tray of any size, such as a 30-well collection tray 192 or a 96-well collection tray 194, or the receptacle may be an envelope 198 or other bulk container. Depending on the choice of receptacle, the corresponding intermediate tray 200, 200' (shown in FIGS. 8 and 10) or funnel attachment 196 (shown in FIG. 14) may be used to install the receptacle onto the seed collecting platform 190, as described above. The chosen receptacle may first be scanned (e.g., via the scanner 150) to confirm that the appropriate receptacle will be used for the particular job and to provide the controller 300 and/or the processor 305 with further inputs, for example, for positioning the seed collecting platform 190 to collect the selected seeds in the appropriate cavities 193, 195 of a collection tray 192, 194.

Once the seed container 120 and the receptacle 140 are in place, the user may start the job, e.g., via the display 310. Through the various inputs, the controller 300 and/or the processor 305 have received, among other things, a designation of the seeds to be selected and, in some cases, instructions regarding where to put the selected seeds. For example, if a collection tray 192, 194 is used, the controller 300 may have instructions to place the selected seeds sequentially in each cavity 193, 195 of the collection tray, or in only certain cavities of the collection tray.

Referring again to FIG. 16, the controller 300 may be configured to actuate one or more of the seed selectors 160, such as via a bank of solenoid valves 170, to expel a selected seed from a corresponding compartment 122 of the seed container 120. The seed selectors 160 may thus be configured to automatically select a plurality of seeds substantially simultaneously. For example, in the case of an envelope 198 or other bulk container, multiple seed selectors 160 may be actuated at the same time to expel multiple corresponding seeds, thereby increasing the speed and efficiency of the selection process. In other cases, such as those in which the selected seeds must be re-configured into a collection tray 192, 194, the array of seed selectors 160 may be configured to automatically select a plurality of seeds in rapid succession. For example, as described below, although each seed may need to be selected individually for transfer to a corresponding cavity 193, 195 of the collection tray 192, 194, the seed collecting platform 190 may be directed to rapidly move (e.g., by the controller 300) from one position to the next to allow the seed collecting platform to receive the next selected seed. Thus, the individual seed selectors 160 may be actuated in rapid succession, for example with only 2 to 3 seconds between actuations, or just enough time to allow the selected seed to fall into the collection tray before a new seed is selected. In one embodiment, for example, the controller 300 may be configured to select all 96 seeds from a 96-compartment seed container in rapid succession.

Accordingly, the controller 300 may also be configured to direct movement of the seed receiving platform 130 to move the seed container 120 into alignment with the array of seed selectors 160 based on the designation of seeds to be selected to enable expulsion of the selected seeds. Thus, for example, if seeds from the third and fourth rows of the seed container 120 are to be selected, the seed receiving platform 130 may be instructed to move such that the third and fourth rows of the seed container are positioned under the two rows of seed selectors 160 in the depicted embodiment. As described above, the actual movement of the seed receiving platform 130 may be done through the driving of belts 134 that pull the seed receiving platform 130 along tracks 136, shown in FIG. 5, or by any other mechanism as will be recognized by those skilled in the art in view of this disclosure.

Similarly, in cases where the receptacle is a collection tray 192, 194, the controller 300 may be configured to direct movement of the seed collecting platform 190 to move the seed collecting platform (and, as a result, the collection tray) into alignment with the transfer member 180 to enable collection of the selected seeds into a corresponding cavity 193, 195 of the collection tray, as shown in FIG. 7, for example. The controller 300 may, for example, actuate belts and/or motors to drive the seed collecting platform 190 and/or platform 240 along corresponding first and second tracks 230, 250 (shown in FIG. 12) to position the collection tray 192, 194 such that the appropriate cavity 193, 195 is located under the opening 184 of the transfer member 180, and the selected seeds can be deposited in the correct configuration according to the received inputs.

In this regard, the controller 300 may be configured to direct the selection of seeds from more than one seed container 120 and automatically transfer the selected seeds to a single receptacle. For example, a particular job may require that 10 seeds be selected from a first seed container 120, 8 seeds be selected from a second seed container, and 5 seeds be selected from a third seed container for re-configuring into a 30-well collection tray 192. In this case, once the first 10 seeds have been selected, the user may be prompted to remove the first seed container 120 from the dispensing area 110 and replace it with the second seed container. Likewise, once the next 8 seeds have been selected and deposited in the appropriate cavities 193, the user may again be prompted to remove the second seed container 120 and replace it with the third.

Furthermore, in some embodiments, the processor 305 may be configured to associate each selected seed with the respective cavity 193, 195 of the collection tray 192, 194 receiving the selected seeds or to associate a number of selected seeds with a particular envelop 198 or other bulk container. Thus, for example, the designation received by the controller 300 and used to select the appropriate seed may be associated with a designation of the particular cavity 193, 195 into which the selected seed was deposited. In other words, the data identifying the compartment 122 from which the selected seed was expelled, along with data identifying the particular cavity 193, 195 into which the selected seed was deposited, may be recorded in a file stored in the apparatus 100 or on a server, computer, or device in communication with the apparatus. In this way, the particular characteristics of each seed can be monitored and tracked, even after re-configuration of the selected seeds for future use by accessing the stored information.

As will be recognized by one skilled in the art, some of the tasks described above as being performed by the controller 300 may also or instead by performed by the processor 305. In addition, the processor 305 need not physically reside in the apparatus 100, but may in some cases communicate with the apparatus (e.g., with the controller 300 of the apparatus) via a wired or wireless network connection.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus for selecting at least one seed from a group of seeds contained in a seed container having a plurality of compartments, each compartment configured to hold a seed, the apparatus comprising:
    a seed receiving platform configured to receive the seed container;
    an array of seed selectors, wherein each seed selector is configured to expel a selected seed from a corresponding compartment of the seed container;
    a receptacle for collecting selected seeds expelled from the seed container;
    a transfer member configured to transfer each selected seed from the seed container to the receptacle;
    a controller configured to receive a designation of seeds to be selected, wherein the designation is associated with the predetermined characteristic of the selected seed; and
    a seed collecting platform configured to engage the receptacle,
    wherein the array of seed selectors is configured to automatically select at least one seed having a predetermined characteristic for transfer to the receptacle, and
    wherein the receptacle is a collection tray defining a plurality of cavities each configured to receive a selected seed, wherein the seed collecting platform is configured to receive an intermediate tray that is configured to hold the collection tray, and wherein the controller is configured to direct movement of the seed collecting platform to move the seed collecting platform into alignment with the transfer member to enable collection of each selected seed into a corresponding cavity of the collection tray.

2. The apparatus of claim 1 further comprising a processor, wherein the processor is configured to associate each selected seed with the corresponding cavity of the collection tray.

3. The apparatus of claim 1, wherein the array of seed selectors is configured to automatically select a plurality of seeds substantially simultaneously.

4. The apparatus of claim 1, wherein the array of seed selectors is configured to automatically select a plurality of seeds in rapid succession.

5. The apparatus of claim 1, wherein the apparatus includes at least one scanner configured to identify one or more of the seed container and the receptacle.

6. A method of selecting one or more seeds from a group of seeds contained in a seed container having a plurality of compartments, each compartment configured to hold a seed, the method comprising:
    receiving the seed container on a seed receiving platform;
    expelling a selected seed from a corresponding compartment of the seed container through actuation of one of an array of seed selectors; and
    automatically transferring each selected seed from the seed container to a receptacle, wherein each selected seed has a predetermined characteristic,
    wherein the receptacle is a collection tray, and wherein the step of automatically transferring comprises moving the collection tray into alignment with a transfer member to enable collection of each selected seed into a corresponding cavity of the collection tray.

7. The method of claim 6, wherein the step of receiving a seed container comprises receiving more than one seed container and automatically transferring each selected seed from the seed containers to a single receptacle.

8. The method of claim 6, wherein the step of expelling a selected seed comprises expelling the selected seed through contact with the seed container only.

9. The method of claim 6, wherein the step of expelling a selected seed comprises automatically expelling a plurality of seeds substantially simultaneously.

10. The method of claim 6, wherein the step of expelling a selected seed comprises automatically expelling a plurality of seeds in rapid succession.

11. The method of claim 6 further comprising receiving a designation of one or more seeds to be selected, wherein the designation is associated with the predetermined characteristic.

12. The method of claim 6 further comprising moving the seed receiving platform such that the seed container is in alignment with the array of seed selectors based on the designation of seeds to be selected.

* * * * *